(12) United States Patent
Ratna et al.

(10) Patent No.: US 9,751,913 B2
(45) Date of Patent: Sep. 5, 2017

(54) METAMATERIAL OPTICAL ELEMENTS SELF-ASSEMBLED ON PROTEIN SCAFFOLDS

(71) Applicants: Banahalli R. Ratna, Alexandria, VA (US); Carissa M. Soto, Alexandria, VA (US); Ronald W. Rendell, Washington, DC (US); Jake Fontana, Alexandria, VA (US); Jeffrey R. Deschamps, Laurel, MD (US)

(72) Inventors: Banahalli R. Ratna, Alexandria, VA (US); Carissa M. Soto, Alexandria, VA (US); Ronald W. Rendell, Washington, DC (US); Jake Fontana, Alexandria, VA (US); Jeffrey R. Deschamps, Laurel, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 133 days.

(21) Appl. No.: 14/207,807

(22) Filed: Mar. 13, 2014

(65) Prior Publication Data
US 2014/0194602 A1 Jul. 10, 2014

Related U.S. Application Data

(63) Continuation-in-part of application No. 13/349,189, filed on Jan. 12, 2012, now Pat. No. 8,831,386.

(51) Int. Cl.
*H01B 1/02* (2006.01)
*C07K 14/00* (2006.01)
*C07K 14/005* (2006.01)
*H01B 1/12* (2006.01)
*B82Y 20/00* (2011.01)
*G01N 21/552* (2014.01)
(Continued)

(52) U.S. Cl.
CPC ............ *C07K 14/005* (2013.01); *B82Y 20/00* (2013.01); *G01N 21/554* (2013.01); *H01B 1/02* (2013.01); *H01B 1/12* (2013.01); *B82Y 30/00* (2013.01); *B82Y 40/00* (2013.01)

(58) Field of Classification Search
CPC ... H01B 1/00; H01B 1/08; H01B 1/02; H01B 1/12; C08L 89/00; B82Y 30/00; B82Y 40/00; C07K 14/01
See application file for complete search history.

(56) References Cited

U.S. PATENT DOCUMENTS 8,019,555 B1 * 9/2011 Ratna ................. C12N 7/00
435/5
8,831,386 B2 * 9/2014 Ratna ................. G01N 21/554
359/244

OTHER PUBLICATIONS

Zahr et al "Solution phase gold nanorings on a viral protein template", Nano Letters 2012, 12, 629-633.*
(Continued)

*Primary Examiner* — Mark Kopec
(74) *Attorney, Agent, or Firm* — US Naval Research Laboratory; Roy Roberts

(57) ABSTRACT

A genetically modified cowpea mosaic virus (CPMV) protein capsid serves as a scaffold for metal nanoparticles, preferably gold nanospheres, of 15 nm to 35 nm, creating plasmonic nanoclusters. The self-assembled nanoclusters gave rise to a 10-fold surface-averaged enhancement of the local electromagnetic field. Other viral capsids or virus-like proteins may also serve as such scaffolds.

8 Claims, 15 Drawing Sheets

(51) Int. Cl.
B82Y 40/00 (2011.01)
B82Y 30/00 (2011.01)

(56) References Cited

OTHER PUBLICATIONS

Gillitzer et al "Chemical modification of a viral cage . . . ", Chem. Commun., 2002, 2390-2391.*
Fontana et al "Virus-Templated Plasmonic Nanoclusters . . . ", small 2014, 10, No. 15, 3058-3063 (including Supporting Information sheets).*
Alú and Engheta (2009) the quest for magnetic plasmons at optical frequencies. Optics Express 17, 5723-5731.
Bastus et al., "Kinetically Controlled Seeded Growth Synthesis of Citrate-Stabilized Gold Nanoparticles of up to 200 nm: Size Focusing versus Ostwald Ripening" Langmuir 2011, 27, 11098-11105.
Blum et al., "Cowpea Mosaic Virus as a Scaffold for 3-D Patterning of Gold Nanoparticles" Nano Lett., vol. 4, No. 5, (2004) p. 867.
Blum et al., "Templated self-assembly of quantum dots from aqueous solution using protein scaffolds" Nanotechnology 17 (2006) 5073-5079.
Douglas, T.; Young, M. "Viruses: Making friends with old foes." Science 2006, 312, 873-875.
DuFort and Dragnea, Annu. Rev. Phys. Chem. 2010.61:323-344. Bio-Enabled Synthesis . . . .
Johnson J., Lin T., Lomonossoff G. (1997) Presentation of heterologous peptides on plant viruses: Genetics, structure, and function. Annu. Rev. Phytopathol. 35, 67-86.
Lee et al. "Viruses and Virus-Like Protein Assemblies—Chemically Programmable Nanoscale Building Blocks" Nano Res (2009) 2: 349 3649.
Medintz et al., "Decoration of Discretely Immobilized Cowpea Mosaic Virus with Luminescent Quantum Dots" Langmuir 2005, 21, 5501-551.
Montague et al., "Recent advances of cowpea mosaic virus-based particle technology" Human Vaccines 7:3, 383-390; Mar. 2011.
Nanogold product information, Nanoprobes Inc., Nov. 2006.
Schmitt, J. et al., Adv. Mater. 1997, 9, 61, "Metal Nanoparticle/Polymer Superlattice . . . ".
Shafiei F., Monticone E, Le K.Q., Liu X.-X., Hartsfield T., Alu A., Li X. (2013) a subwavelength plasmonic metamolecule exhibiting magnetic-based optical Fano resonance. Nat Nano 8, 95-99.
Soto et al., "Separation and recovery of intact gold-virus complex by agarose electrophoresis and electroelution: Application to the purification of cowpea mosaic virus and colloidal gold complex" Electrophoresis 2004, 25, 2901-2906.
Toussaint L., Bertrand L., Hue L., Crichton R.R., Declercq J.P. (2007) Hight-resolution X-Ray structures of human apoferritin H-chain mutants corrrelated with their activity and metal-binding sites J. Mol. Biol. 365, 440-452.
Urban et al., "Three-Dimensional Plasmonic Nanoclusters" Nano Lett., 2013, 13 (9), pp. 4399-4403.
Wang, Q., Kaltgrad, E., Lin, T., Johnson, J. E. & Finn, M. G. Natural Supramolecular Building Blocks: Wild-Type Cowpea Mosaic Virus. Chemistry & Biology 9, 805-811 (2002).
Wang, Q., Lin, T., Tang, L., Johnson, J.E., and Finn, M.G. (2002). "Icosahedral virus particles as addressable nanoscale building blocks." Angew. Chem. Int. Ed. 41, 459-462.
Li et al. "Three-Dimensional Gold Nanoparticle Clusters with Tunable Cores Templated by a Viral Protein Scaffold" S Small 2012, 8, No. 24, 3832-3838.
Suzuki et al. "Preparation and catalytic reaction of Au/Pd bimetallic nanoparticles in Apo-ferritin" Chem. Commun., 2009, 4871-4873.
K. H. Su, Q. Fl Wei, X. Zhang, J. J. Mock, D. R. Smith, and S. Schultz, "Interparticle coupling effects on plasmon resonances of nanogold particles," Nano Lett. 3, 1087-1090 (2003).
J. Fontana, W. J. Dressick, J. Phelps, J. E. Johnson, R. W. Rendell, T. Sampson, B. R. Ratna, and C. M. Soto, "Virus-Templated Plasmonic Nanoclusters with Icosahedral Symmetry via Directed Self-Assembly," Small 10, 3058-3063 (2014).

* cited by examiner

METAMATERIAL OPTICAL ELEMENTS SELF-ASSEMBLED ON PROTEIN SCAFFOLDS

CROSS-REFERENCE TO RELATED APPLICATIONS

This application claims the benefit as a continuation-in-part of U.S. patent application Ser. No. 13/349,189 filed on Jan. 12, 2012, which is incorporated herein by reference in its entirety.

BACKGROUND

Material having electric permittivity and magnetic permeability that are simultaneously negative at certain frequencies have a negative index of refraction for these frequencies. Plasmonic ring resonators (PRRs), which include split ring resonators (SRRs), have been used to create materials having a negative index of refraction, also termed negative index materials (NIMs). See, for example, commonly-owned U.S. Pat. Nos. 7,646,524, 7,683,444, and 7,808,722 as well as *Fast Light, Slow Light and Left-Handed Light*, P. W. Milonni, Institute of Physics Publishing (2005), each of which is incorporated herein by reference in its entirety.

NIMs have several applications, for example in the production of superlenses, which overcome the diffraction limit by enhancing and recovering the evanescent waves emitted by an object to allow resolution of features much smaller than the incident wave. Although NIMs have been produced in the microwave frequencies, it remains a challenge to produce NIMs that operate in the visible/near infrared spectrum due to the required size of the resonant structures. Moreover, it has been proposed that, in theory, a ring of metallic nanoparticles can create magnetic oscillations at optical frequencies by the formation of displacement currents excited from an optical source. Such optically active structures can produce a permeability value different from unity at optical and near infrared frequencies.

The various structures necessary for realizing such optical phenomena require nanoscopic control of structural details. Nano-lithographic techniques to create such structures with features in the range of 10 or 10 s of nanometers are time consuming, expensive and suffer from a lack of registration over extended length scales. Thus, a need exists for fabrication of high resolution nanoscale metamaterial structures.

BRIEF SUMMARY

In one embodiment, a nanocluster comprises a cowpea mosaic virus (CPMV) protein capsid, the protein genetically modified to incorporate a plurality of cysteine residues providing thiol groups on an exterior surface of the capsid, and a plurality of metal nanoparticles with a size between 15 nm and 35 nm bound to the thiol groups.

In a further embodiment, a method of preparing nanoclusters includes providing metal nanoparticles with a size between 15 nm and 35 nm, and contacting a viral protein capsid with the metal nanoparticles in a solution comprising a chelator, thereby obtaining nanoclusters comprising the metal nanoparticles bound to the viral protein capsid. In a yet further embodiment, the viral protein capsid is that of cowpea mosaic virus (CPMV) and is in a state of being genetically engineered to incorporate a plurality of cysteine residues providing thiol groups on an exterior surface of the capsid.

In another embodiment, a nanocluster includes a viral capsid and a plurality of metal nanoparticles with a size between of 15 nm to 35 nm bound to the thiol groups.

BRIEF DESCRIPTION OF THE DRAWINGS

FIG. 3 contains micrographs of His-TMV-CP and WT-TMV-CP samples in 100 mM buffer after 4 days at 4° C. at various pHs.

FIG. 4 shows His-TMV-CP and WT-TMV-CP control samples in 400 mM buffer after 4 days at 4° C. at various pHs.

FIG. 6A shows 139Cys-His-TMV-CP after reaction and purification. FIG. 6B shows an atomic force microscopy (AFM) image of purified 139Cys-His-TMV-CP.

FIG. 8A shows His-TMV-CP disk-Au complexes. FIG. 8B uses the same image as FIG. 8A but with superimposed schematic images of the size and shape of the expected 20 nm disks.

FIG. 9A shows His-TMV-CP rods that were assembled in solution at 400 mM buffer concentration pH 5.0 and stained with uranyl acetate for visualization purposes. FIG. 9B shows His-TMV-CP rods after reaction with Ni-NTA-Nanogold and the sample was not stained.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials that are similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the term "plasmonic ring resonator" refers to a plasmonic waveguide in the shape of a ring and comprising closely spaced metallic material (for example, gold or silver). Although the metallic material is closely spaced along the ring, one or more small gaps may exist (i.e., the ring may be optionally be split and/or disordered, for example to form a split ring resonator). A plasmonic ring resonator generally has a diameter of no greater than 100 nm, with certain embodiments of plasmonic ring resonators having diameters of about 30, 29, 28, 27, 26, 25, 24, 23, 22, 21, or 20 nm.

As used herein, the terms "tobacco mosaic virus coat protein" (TMV-CP) and "cowpea mosaic virus" (CPMV) denote the wild-type versions of these proteins, as well as chemically and/or genetically modified variants thereof, unless clearly noted otherwise.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

Tobacco Mosaic Virus Coat Protein

Tobacco mosaic virus coat protein (TMV-CP) can be used as a nanosized scaffold for nanoscale structures. Seventeen individuals coat proteins assemble to form a single 18 nm disk or ring. See FIG. 1. These disks normally stack around the TMV RNA genome to form a tube that is 300 nm long and 18 nm in diameter. See, e.g., Bruckman et al., ACS Nano, Vol. 5, No. 3, pp. 1606-1616 (2011) and O. K. Zahr and A. S. Blum, "Solution Phase Gold Nanorings on a Viral Protein Template," *Nano Lett.*, web publication dated Dec. 26, 2011, each of which is incorporated herein by reference.

Figure 1:
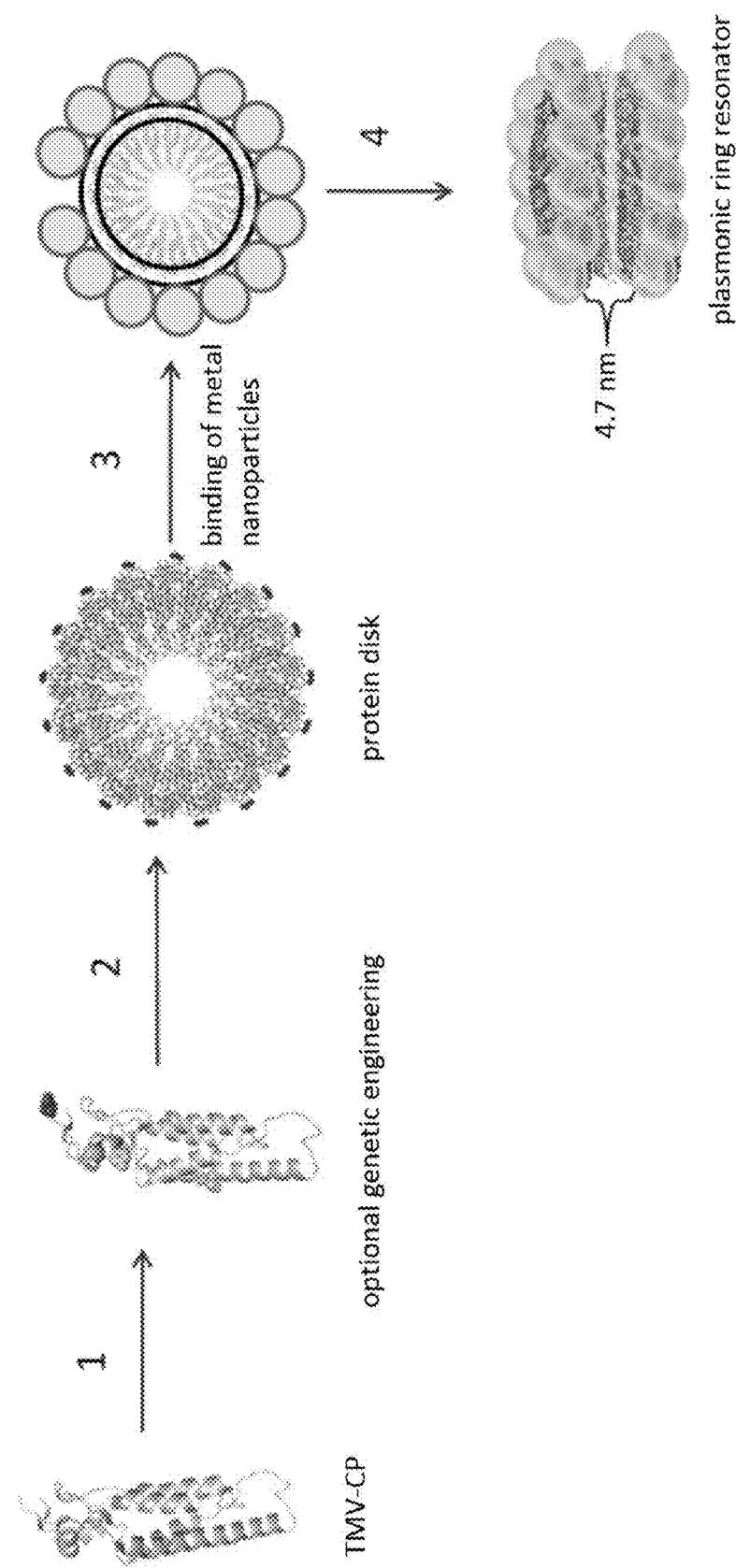
FIG. 1 is a schematic of how illustrative embodiments of the plasmonic ring resonators were created by self-assembly. Based on the protein structure of tobacco mosaic virus coat protein (TMV-CP) genetic engineering was performed to generate proteins with available chemical handles for nanoparticle binding (1). After protein production the proteins self-assemble in solution to form disk-like structures of about 18 nm in diameter (2). Disks are mixed with nanoparticles (3) that carry proper chemistries for binding. Resultant disks-nanoparticle complexes form plasmonic ring resonators (4).

The TMV coat protein can be genetically modified as described herein to incorporate polyhistidine, which (1) desirably improves the stability of the disk form of the protein, and (2) provides a binding site for metals, so that when assembled in a disk, 17 metal-binding sites are present. The present inventors have used polyhistidine-modified TMV coat protein as a protein scaffold to form metal-decorated disks of 20 to 30 nm diameter, which are expected to serve as plasmonic ring resonators and otherwise provide utility in building nanostructured circuit elements (NSE) with nanoscale features. A schematic illustrating an exemplary embodiment is seen in FIG. 1. Although genetic engineering to incorporate polyhistidine is a preferred embodiment, wild-type coat protein may be employed, for example with one or more chemical modifications. For example, wild-type protein may be chemically modified to include polyhistidine and/or other functional elements such as a peptide linker.

The wild-type TMV coat protein (WT-TMV-CP) can be isolated as three major assembled components in the absence of the TMV genome: protein A (a dynamic equilibrium between monomers, trimers, and pentamers of WT-TMV-CP), disks consisting of 34 monomers (also known as the 20S structure), and helical rods of various lengths. WT-TMV-CP assemblies in solution can be controlled to favor protein A, disks, or rods depending on the pH and ionic strength. Previous work involving modification of the WT-TMV-CP either through genetic engineering or chemical modifications did not significantly change the equilibrium conditions between the various assemblies. However, the present inventors have found that histidine-modified TMV coat protein was found to significantly affect the self-assembly as compared to the wild-type coat protein, a fact that can be exploited to prepare nanostructured circuit elements (NSEs) under a wider variety of conditions. The incorporated His tag further provides a chemical handle to allow for binding of certain nanoparticles. This allowed the construction of Au-disk structures of about 30 nm in diameter which are expected to produce negative index materials as a component of a three dimensional arrangement.

Previous work on nano-scale structures from TMV-CP did not incorporate the polyhistidine tag, which as described herein was surprisingly found to extend the ability of disk-like structure to exist a broader range of conditions. Such stabilization of the disk-like structure is critical for the construction of the plasmonic ring resonator. After allowing for the metal decorating the 18 nm protein disk, the plasmonic ring resonators are preferably from 20 nm to 30 nm in diameter for obtaining the desired magnetic resonances at optical wavelengths.

As NSEs can be designed and fabricated in the form of nanoscale plasmonic ring resonators, nanoscale coupled plasmonic ring resonators and nanoscale elements containing clusters of metal, insulator and/or semiconductor nanoparticles functional at optical or near infrared frequencies. Optical gain, in the function of the nanostructured circuit elements, can also be introduced by incorporation of dye or other materials that can be pumped separately or as part of a resonant scattering process.

Electromagnetic Response of TMV Nanoparticle Arrays

The electromagnetic response of TMV nanoparticle arrays for both TMV disks and TMV nanorods was evaluated by numerical modeling.

Modeling was performed by numerical simulation using the finite-element code, COMSOL Multiphysics. This code allows construction of the 3-dimensional geometries of the nanoparticles and attachment of these along the virus structure to form arrays of arbitrary design. Material properties are incorporated in terms of the frequency dependent dielectric functions of the metals comprising the nanoparticles and surrounding dielectrics. The electromagnetic fields corresponding to plasmonic excitations in these configurations are found by solving the governing electromagnetic equations with appropriate boundary conditions. The characteristics of the spectra of the localized and propagating plasmon modes can be studied for their dependences on the geometry, configuration and material properties of the nanoparticle structures as well as their method of excitation.

The calculated near-fields of TMV disks indicated that magnetic resonances in the visible are found to be excited in response to an incident plane wave polarized with the applied magnetic field perpendicular to the plane of the disk. The magnetic resonance is found to be governed primarily by loops of electric displacement current around the ring of particles. A variety of particle ring designs were studied which are compatible with the attachment of 3-5 nm Au and Ag nanoparticles on the TMV disks. These can be viewed as distributions of individual particles and dimers placed at different spacings around the circumference of the disk as shown by the three examples (i), (ii), and (iii) in FIG. 2A. The wavelengths of the resonances are found to be close to that of an isolated nanoparticle dimer (shown by the thinner of the solid lines in FIG. 2A) but red-shifted and enhanced due to the plasmonic coupling of closely-spaced particles (shown as "coupled modes" in the figure) or due to ohmic contact between the particles (shown as "contact modes" in the figure). The magnetic resonance response for the various arrays is closely grouped into these two types of modes but differ in detail due to the variety of spacings.

Figure 2A:
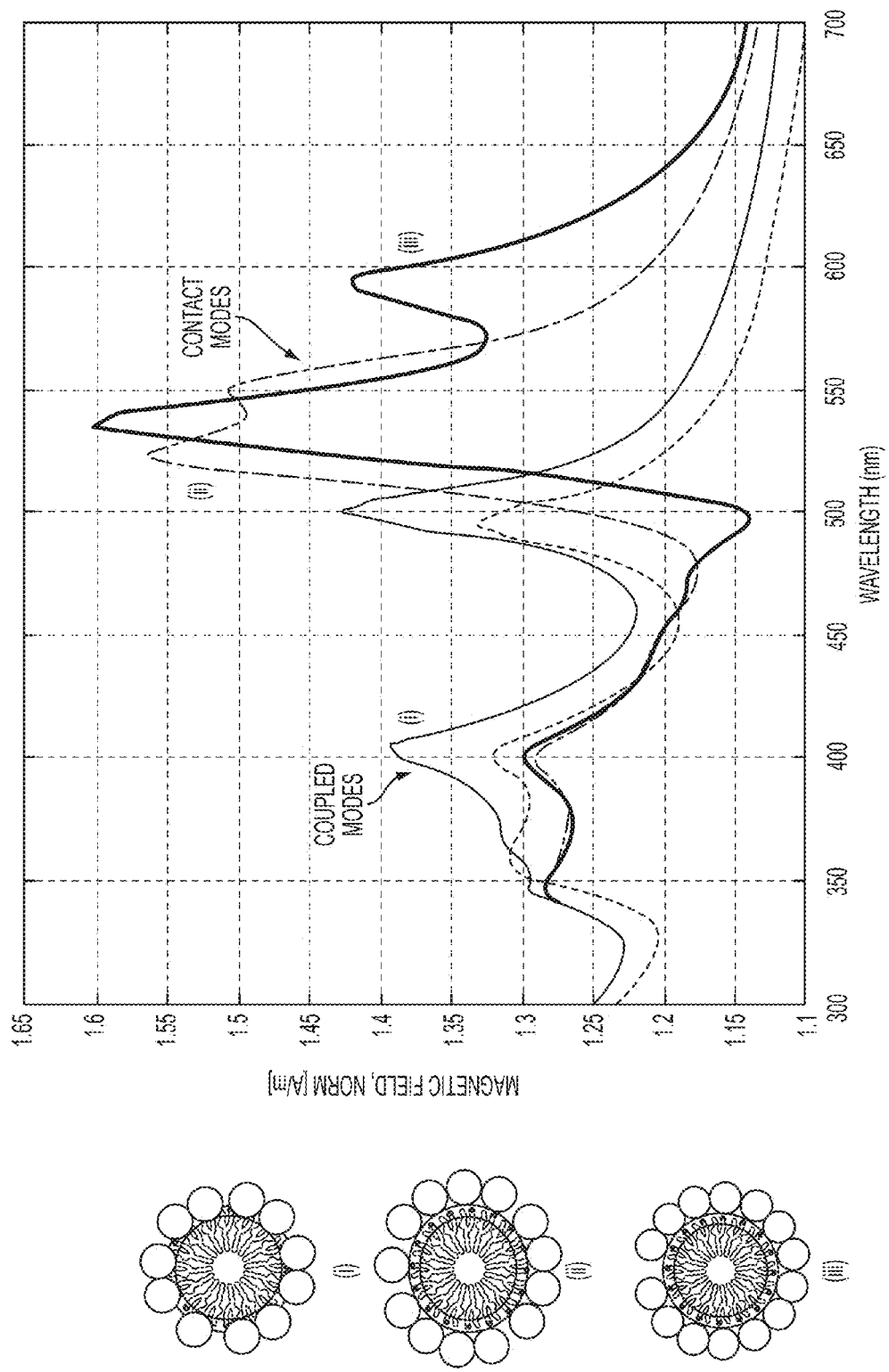
FIG. 2A illustrates modeled results of the magnetic near-field resonance response in the visible for nanoparticle-array TMV disk designs in response to an incident plane-wave with magnetic field perpendicular to the disk plane. The resonances are near those of an isolated dimer (lighter weight lines, solid and with uniform dashes) but enhanced and shifted due to plasmonic coupling and contact coupling.
Figure 2B:
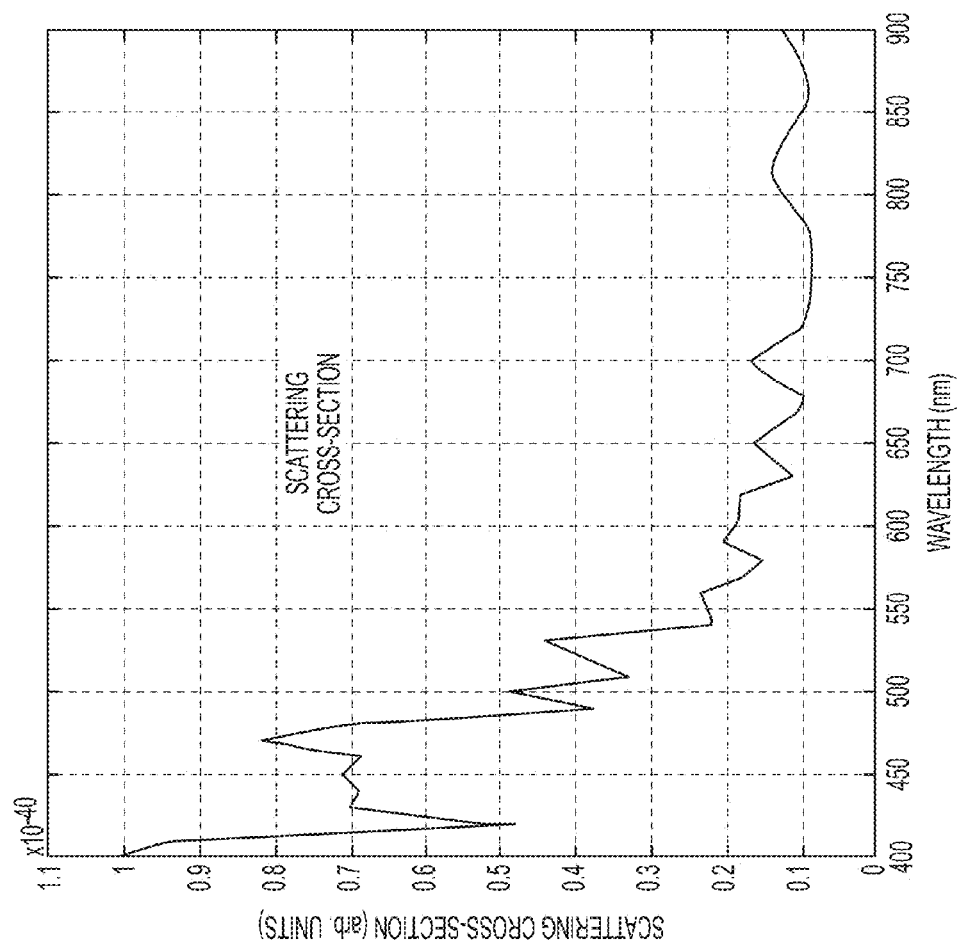
FIG. 2B shows calculated far-field scattering cross-section in the visible of a 500 nm TMV rod coated with an effective-medium representing a random nanoparticle coating and lying on an oxidized Si substrate to an incident plane wave polarized along the length of the rod. The scattering response corresponds both to surface plasmons localized on the TMV rod and to plasmons due to the contact of the TMV rod with the substrate.
Figure 2B:
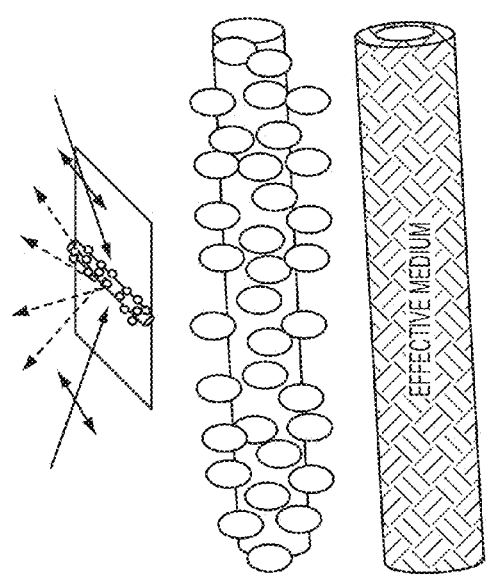

FIG. 2B shows the scattering cross-section in the visible obtained from the calculated far-fields of a nanoparticle-coated 500 nm long TMV nanorod in response to an incident plane wave, using modeled data. This was incident at 11 degrees from the surface with electric field polarized along the length of the rod and the scattered far-fields were collected within a half-angle cone of 64 degrees corresponding to the conditions of dark-field measurements. The nanorod lies on a substrate consisting of 100 nm $SiO_2$ on Si. The random distribution of 6 nm Au nanoparticles on the surface of the rod was represented by an Au/Air Bruggeman effective medium of spherical inclusions. The scattered response of the nanoparticle-coated TMV rod has contributions both due to the localized surface plasmons of the nanoparticles and due to plasmonic modes due to the contact of the TMV rod with the substrate.

Figure 2C:
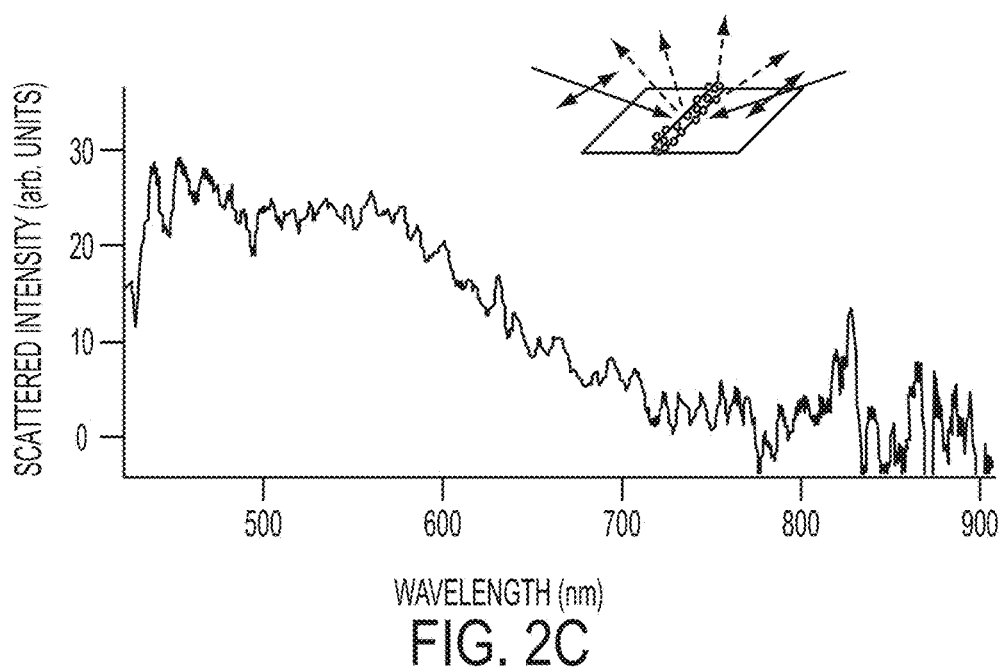
FIG. 2C shows an experimental spectrum obtained from a 500 nm long TMV rod decorated with 6 nm diameter Au NPs.

FIG. 2C shows a single particle scattering spectrum obtained with actual experimental data for a 500 nm long TMV rod decorated with 6 nm diameter Au NPs. The incident light was polarized in the plane and directed in beams perpendicular to the rod.

Figure 2D:
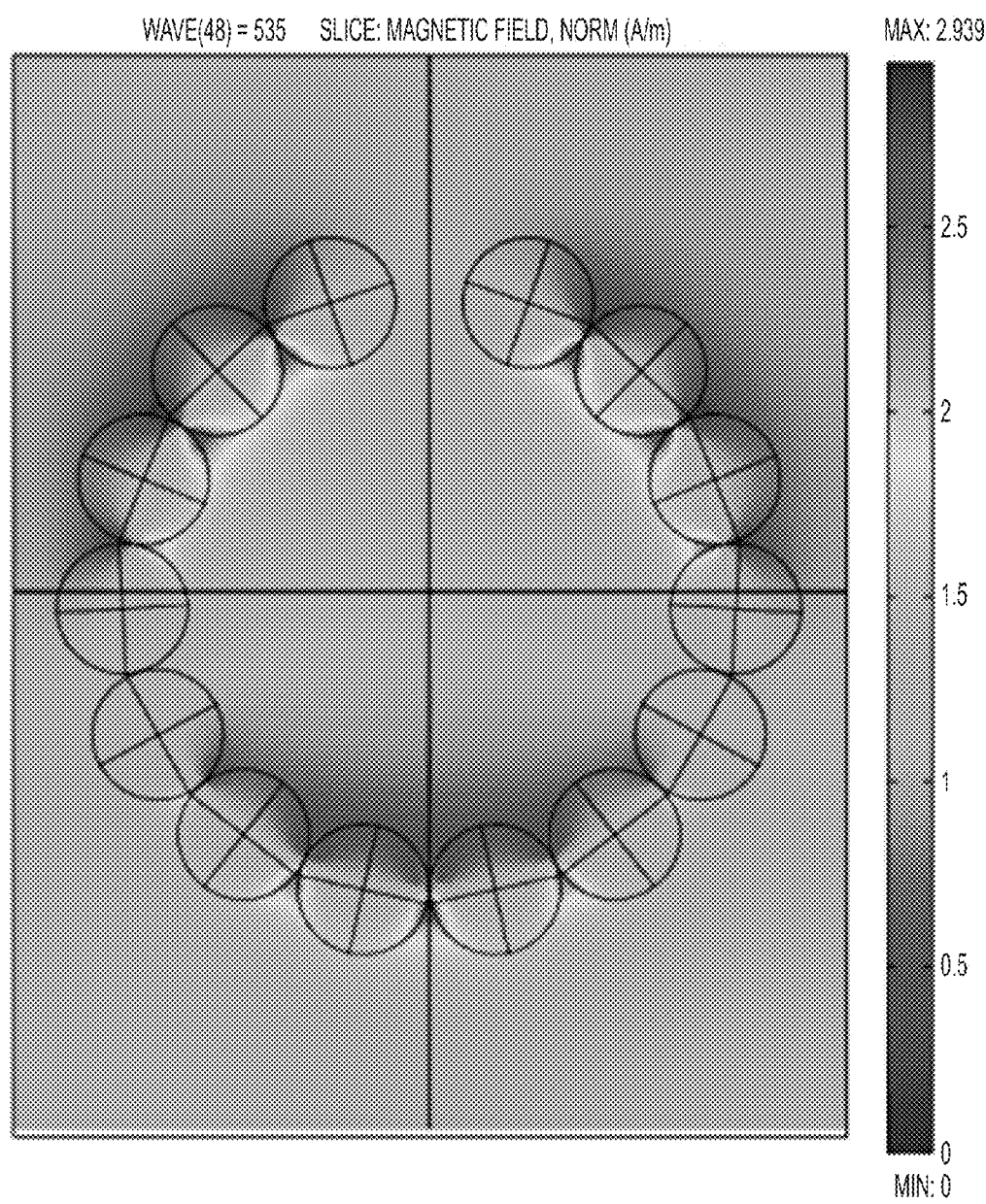
FIG. 2D shows modeled results of the magnetic near-field resonance response in the visible for nanoparticle-array TMV disk designs in response to an incident plane-wave with magnetic field perpendicular to the disk plane, based on the ring configuration depicted in arrangement (iii) of FIG. 2A.

FIG. 2D shows modeled results of the magnetic near-field resonance response in the visible for nanoparticle-array TMV disk designs in response to an incident plane-wave with magnetic field perpendicular to the disk plane, based on the ring configuration depicted in arrangement (iii) of FIG. 2A.

Production of His-TMV-CP

The primers TMVCP F1 (SEQ ID NO: 1) and His-TMV-CP R1 (SEQ ID NO: 2) were used in a PCR reaction using a wild-type TMV coat protein gene product 6 ("gp6") template (comprising SEQ ID NO: 3). Conditions for amplification were 35 cycles of 95° C. for 30 sec, 55° C. for 30 sec, and 68° C. for 30 sec. The resulting amplified fragments were then digested with NdeI and NcoI and were subsequently inserted into pET20b vectors DNA using T4 DNA ligase. The ligation mixture was then electroporated into XL1 Blue and plated on LB plates supplemented with 100 µg/mL of ampicillin for overnight incubation at 37° C. Plasmid DNA was then isolated from three potential positive clones grown on the plates and were sent out for DNA sequencing. The sequence confirmed clone, His-TMV-CP-2 (SEQ ID NO: 4), containing 6×His at C-terminus, was then sub-cloned to the expression host, *E. coli* strain Rosetta2 (DE3)pLysS for protein expression and purification using conventional techniques—details can be found in Bruckman et al., ACS Nano, Vol. 5, No. 3, pp. 1606-1616 (2011). The resulting His-TMV-CP protein was observed at 18.5 kDa on a polyacrylamide gel.

Although this example created a hexahistidine-tagged protein, one of ordinary skill in the art may prepare a protein having an alternate number of histidines in the polyhistidine tag, for example 4, 5, 6, 7, 8, 9, 10, 11, or 12 histidines. For example, genetic engineering might be employed to adjust the gap between two metal-decorated protein disks, which is normally 4.7 nm (see FIG. 1). Polyhistidine could be added at the N terminal end of the protein, or elsewhere, instead of the C terminal end as was done in the example. Other modifications to TMV coat protein are contemplated: for example, a peptide linker to enlarge the CP is expected to increase the diameter of the resulting protein disk—such a peptide might be added at the C terminal end, for example before or after a polyhistidine tag. Such modifications may be performed genetically and/or chemically.

Assembly of his-TMV-CP Disks and Rods

His-TMV-CP stock solution at 1.0 mg/mL was centrifuged for 15 min at 4° C. at 9,300 g. The resulting pellet was recovered and dissolved in minimal 100 mM potassium hydroxide (KOH) added in 20 µL increments. The suspended pellet was incubated at 4° C. for two hours. Protein concentration was determined by using absorbance values of the peak at 278 nm and previously reported extinction coefficient ($\epsilon$=1.3 mL mg$^{-1}$cm$^{-1}$). The concentration of His-TMV-CP was set to 1.7 mg/ml and dialyzed against 10 mM or 100 mM potassium/sodium phosphate at pH 8.5 at 4° C. in a Slide-A-Lyzer MINI dialysis unit (10 kDa MWCO). At this stage the protein is refolded into the protein A form. Protein samples at pH 8.5 were dialyzed for 24 hr at 4° C. against buffers at pH values: 8.0, 7.0 or 6.0 at the desired ionic strength.

Figure 3:
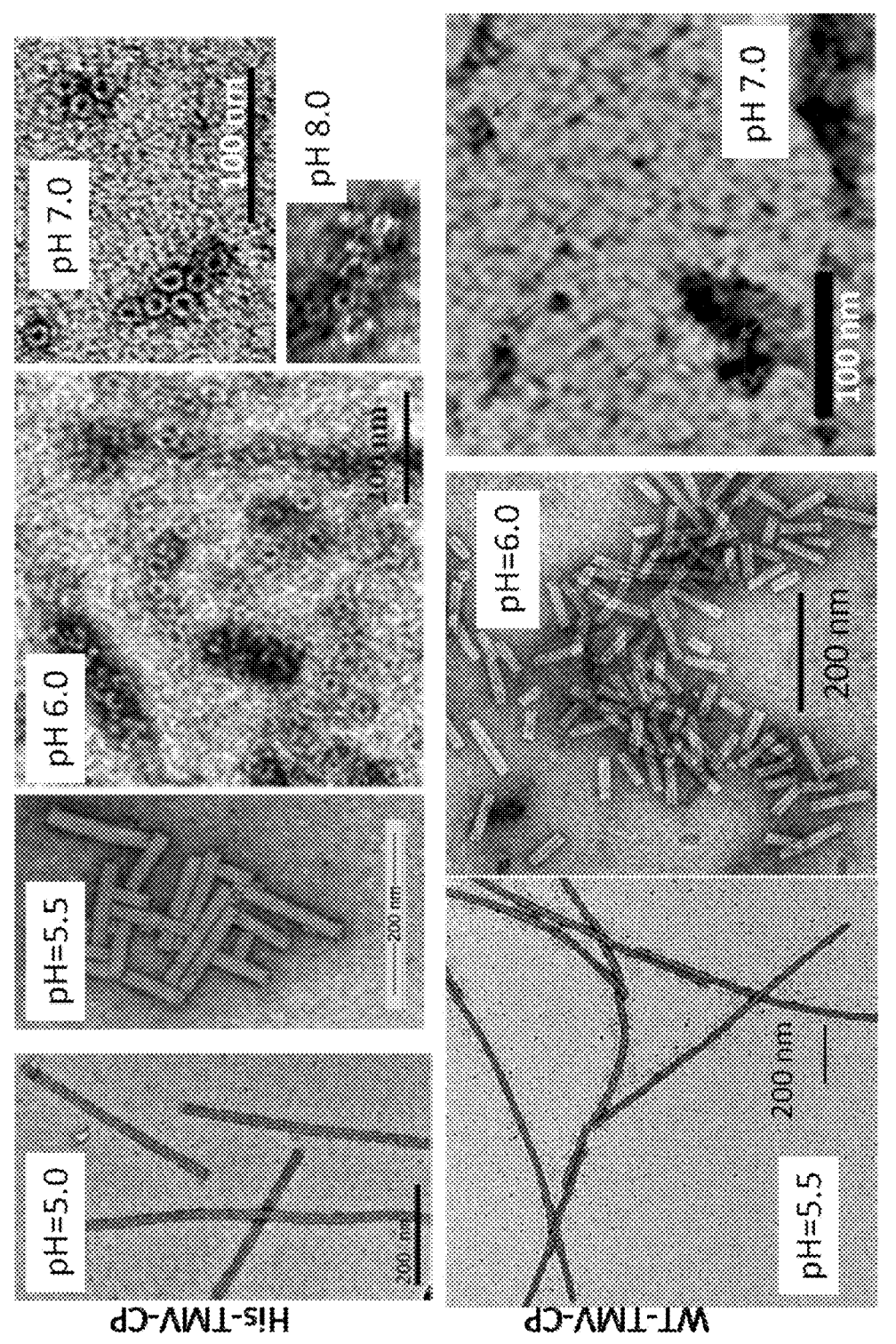

For the assembly of rods a protein solution in 10/100 mM phosphate buffer pH 8.5 is dialyzed against 10 or 100 mM sodium acetate buffer pH 5.5. FIG. 3 contains micrographs of His-TMV-CP and WT-TMV-CP samples in 100 mM buffer after 4 days at 4° C. at various pHs. As pH increases, the dominant structure changes from rods to disks. This transition occurs at a lower pH for His-TMV-CP (pH 6.0) than for WT-TMV-CP (pH 7.0). In addition, disks are still seen at pH 8.0 for His-TMV-CP, while WT-TMV-CP under the same conditions is in protein A form (arrows in FIG. 3).

Figure 4:
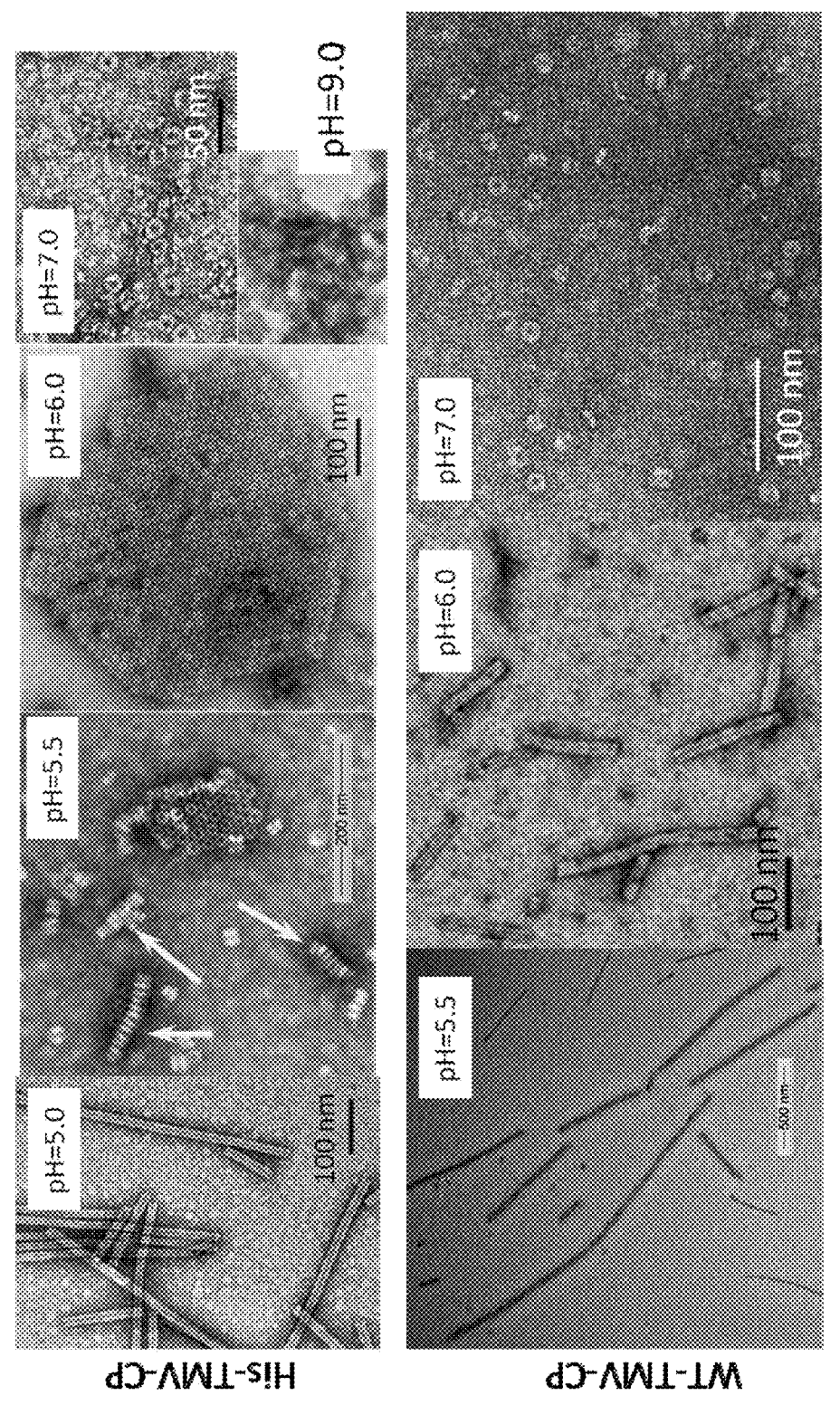

For higher ionic strengths studies protein in 100 mM phosphate buffer pH 8.5 is dialyzed for 24 hr at 4° C. against 400 mM phosphate buffer at pH values: 8.0, 7.0, 6.0 or 400 mM sodium acetate pH 5.5, as seen in FIG. 4 showing His-TMV-CP and WT-TMV-CP samples in 400 mM buffer after 4 days at 4° C. at various pHs. As pH increases, the dominant structure changes from rods to disks. This transition occurs at a lower pH for His-TMV-CP (pH 5.5) than for WT-TMV-CP (pH 7.0). His-TMV-CP shows some additional extended structures. At pH 5.5, there are some stacked disks (indicated by white arrows) and some small hexagonally packed islands. At pH 6.0, hexagonally packed islands are the dominant structure and are much larger in size. At pH 9.0, both TMV-CP proteins are in protein A form.

The image in the top row of FIG. 4 at pH 6 shows a sheet of material that was obtained with His-TMV-CP but could not be obtained with WT-TMV-CP, thus demonstrating the surprising and unexpected improved protein structure obtained when polyhistidine incorporated.

Assessment of Available Chemistries: Amines and Thiols

Figure 5:
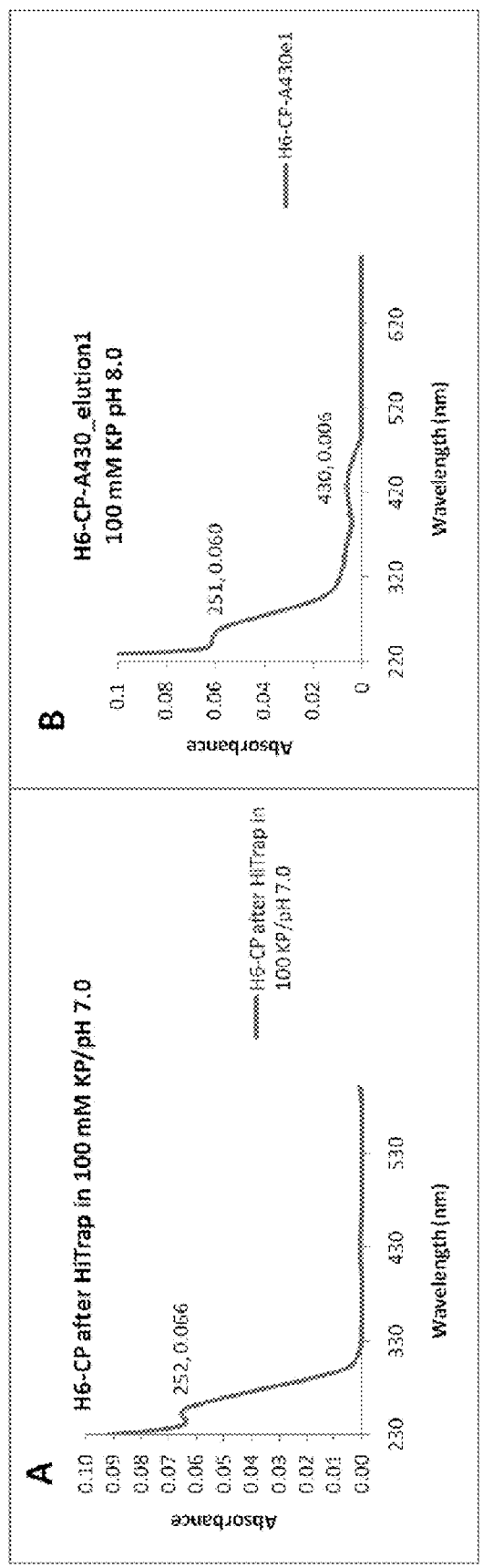
FIGS. 5A and 5B show His-TMV-CP before and after conjugation with a dye having an adsorption peak at 430 nm.

Purified His-TMV-CP (FIG. 5A) was mixed with NHS ester AlexaFluor430 dye and mixed overnight at room temperature, followed by purification with size exclusion chromatography. This resulted in the appearance of a new peak at 430 nm, indicating that the dye had attached to available reactive amines on the His-TMV-CP, as seen in FIG. 5B.

Figure 6:
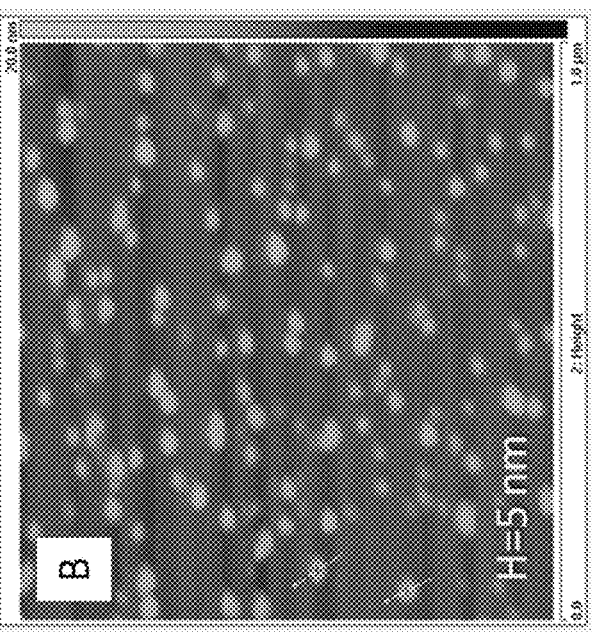
FIGS. 6A and 6B show reactivity of AlexaFluor546 maleimide dye towards solvent-accessible thiols present in 139Cys-His-TMV-CP.
Figure 6:
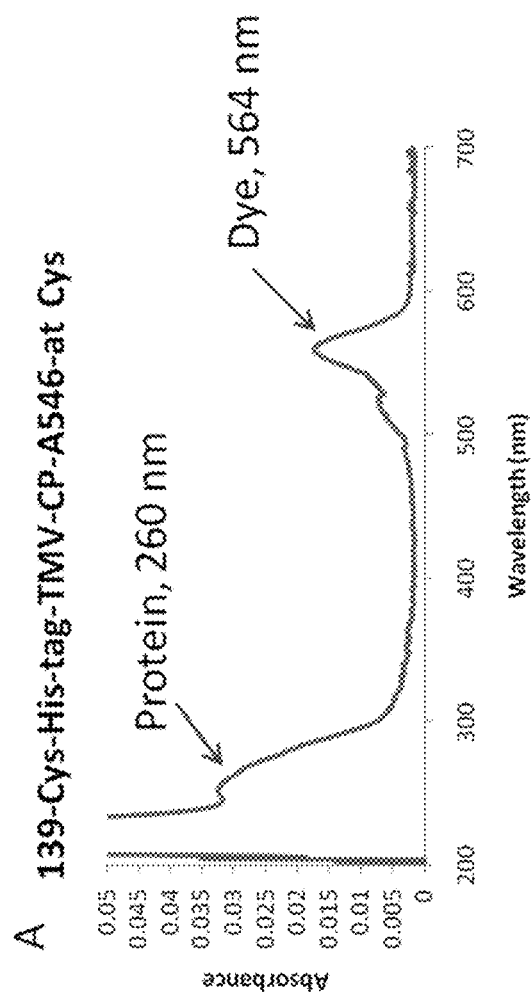

The protein 139Cys-TMV-CP (SEQ ID No: 5) was constructed, comprising a cysteine amino acid which was incorporated by genetic engineering at position 139 of the protein, along with the histidine tags of the His-TMV-CP construct. After expression and purification, the protein was reacted with AlexaFluor 546 maleimide, resulting in a new peak at 546 nm, showing that the dye successfully attached, as seen in FIG. 6A. FIG. 6B shows an atomic force microscopy (AFM) image of purified 139Cys-His-TMV-CP where assembled disks can be seen. The self-assembly properties of the protein into disk-like structure was not been affected by the reaction and purification conditions. FIG. 6B show an atomic force microscopy (AFM) image of assembled disks of purified 139Cys-His-TMV-CP bound to the AlexaFluor 546 maleimide.

Reactivity with Gold Nanoparticles

Figure 7:
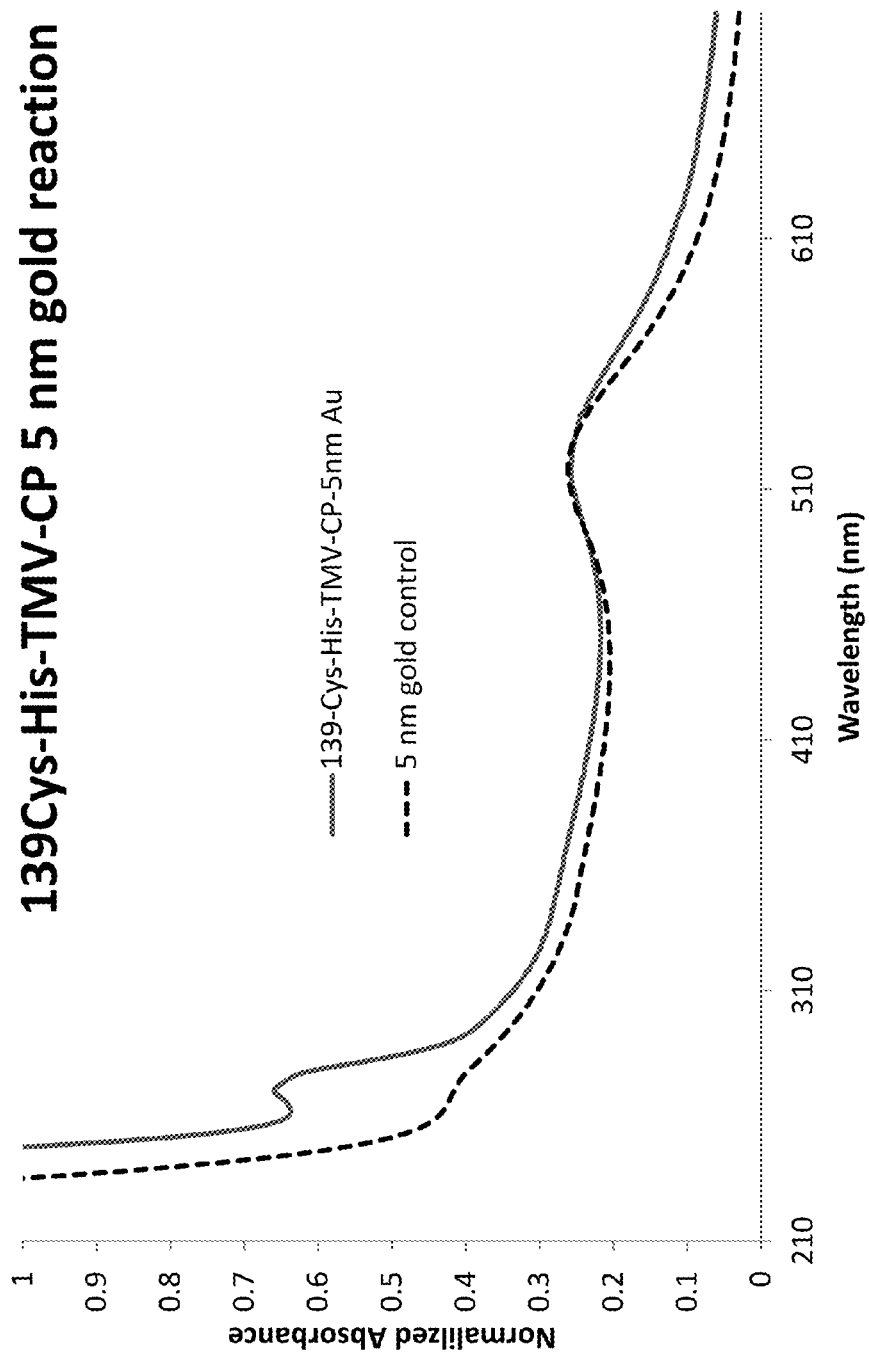
FIG. 7 shows UV-Vis of samples recovered from 1% low melting agarose gel. 139-Cys-TMV-CP gold complex was recovered from the gel using electroelution (solid line). Buffer containing sample was concentrated and analyzed by UV-Vis spectroscopy. Similar procedure was done on the free gold band and used as a control (dashed line). Peak at 530 nm correspond to the plasmon resonance of 5 nm gold and the peak at 278 nm to the protein peak. Data was normalized relative to absorbance at 530 nm.

Samples of 139-Cys-His-TMV-CP were mixed with 5 nm gold and left to react for 5 days at room temperature. The mixture was concentrated by using a Centricon unit with a molecular weight cut-off of 100 kDa and loaded in a 1% low melting agarose. A protein-gold band appeared in the expected position on the gel, and the 139-Cys-TMV-CP gold complex was recovered from the gel using electroelution. Buffer containing sample was concentrated and analyzed by UV-Vis spectroscopy, as seen in FIG. 7.

Reactivity with Ni-NTA-Nanogold

Fifty microliters of His-TMV-CP rods or disks (assembled as described above, with 1.0 mg/ml, 400 mM potassium phosphate buffer pH=6.0 for disks, 400 mM acetate pH=5.0 for rods) were mixed with 50 µL Ni-NTA (nitrilotriacetic acid) coated Au nanoparticles (5 nm, 0.5 µM, from Nanoprobes in Yaphank, N.Y.) for 30 minutes at room temperature prior to spotting the sample on a TEM grid (holey carbon coating, from SPI Supplies). No staining was performed for TEM grid preparation of gold containing samples. Dark spots in TEM images correspond to 5 nm gold. Free gold was not removed from reaction mix prior to TEM imaging. The best mode found for preparing disk-Au complexes was found to be when the disks were assembled at 400 mM buffer concentration at pH 6.0 and the protein to gold ratio was 1:5 (v:v) for the reaction with Ni-NTA-Nanogold, with results seen in FIG. 8. The best rod-Au assemblies were obtained when the rods were assembled at 400 mM buffer concentration pH 5.0, followed by reaction with Ni-NTA-Nanogold at a protein to Au ratio of 1:1 (v:v), results seen in FIG. 9.

Figure 8:
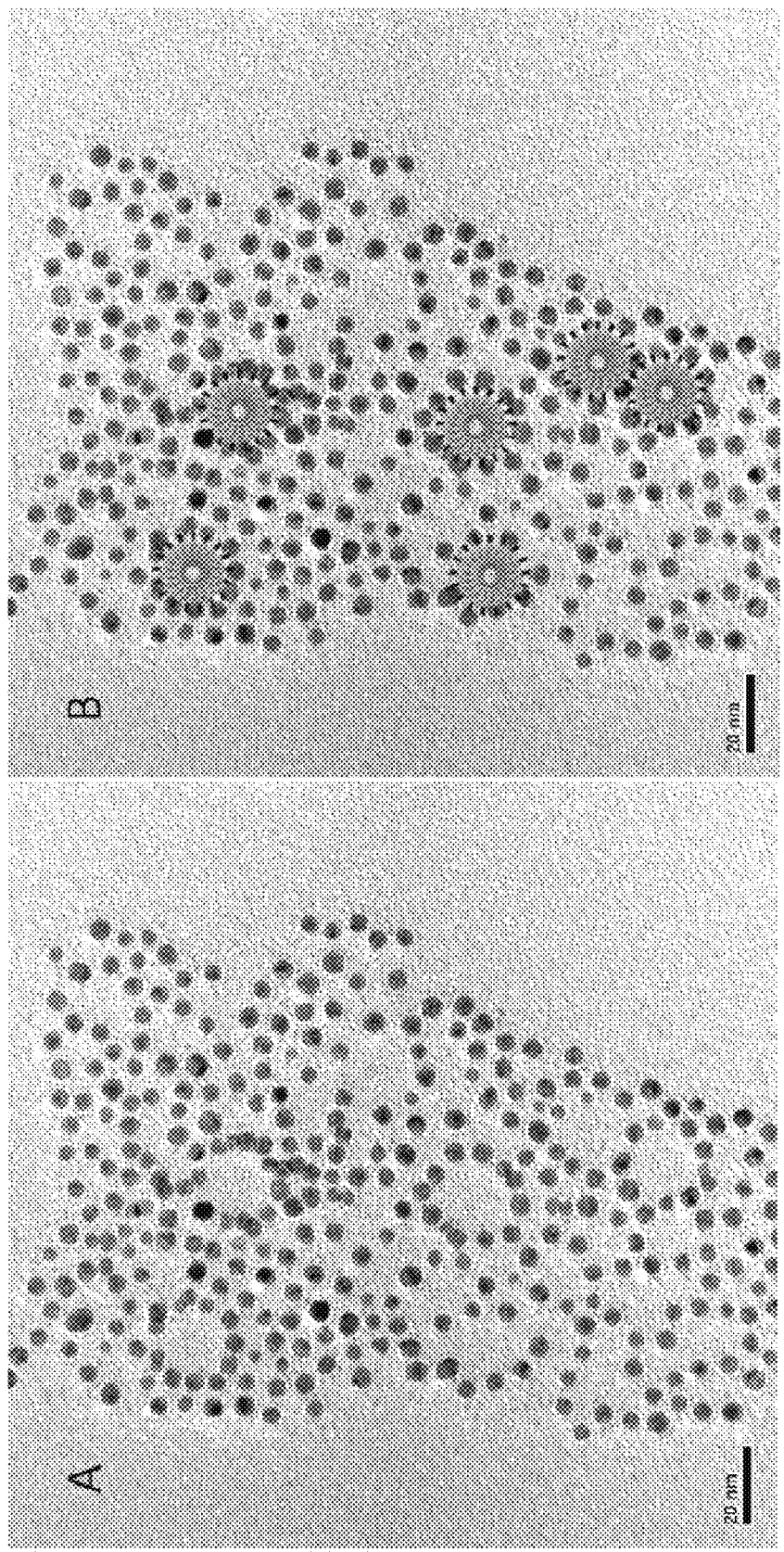
FIG. 8 shows transmission electron micrograph (TEM images) of His-TMV-CP disks-Au complexes. Samples were not stained.

FIG. 8 shows transmission electron micrograph (TEM images) of His-TMV-CP disks-Au complexes. Samples were not stained. FIG. 8A shows His-TMV-CP disk-Au complexes where the dark spots correspond to 5 nm gold. The disk-like structures correspond well with the expected 20 nm diameter for the His-TMV-CP disks. FIG. 8B uses the same image as FIG. 8A but with superimposed schematic images of the size and shape of the expected 20 nm disks. The contour generated by the Au binding to the disks matches well with the expected size and shape of the 20 nm disks.

Figure 9:
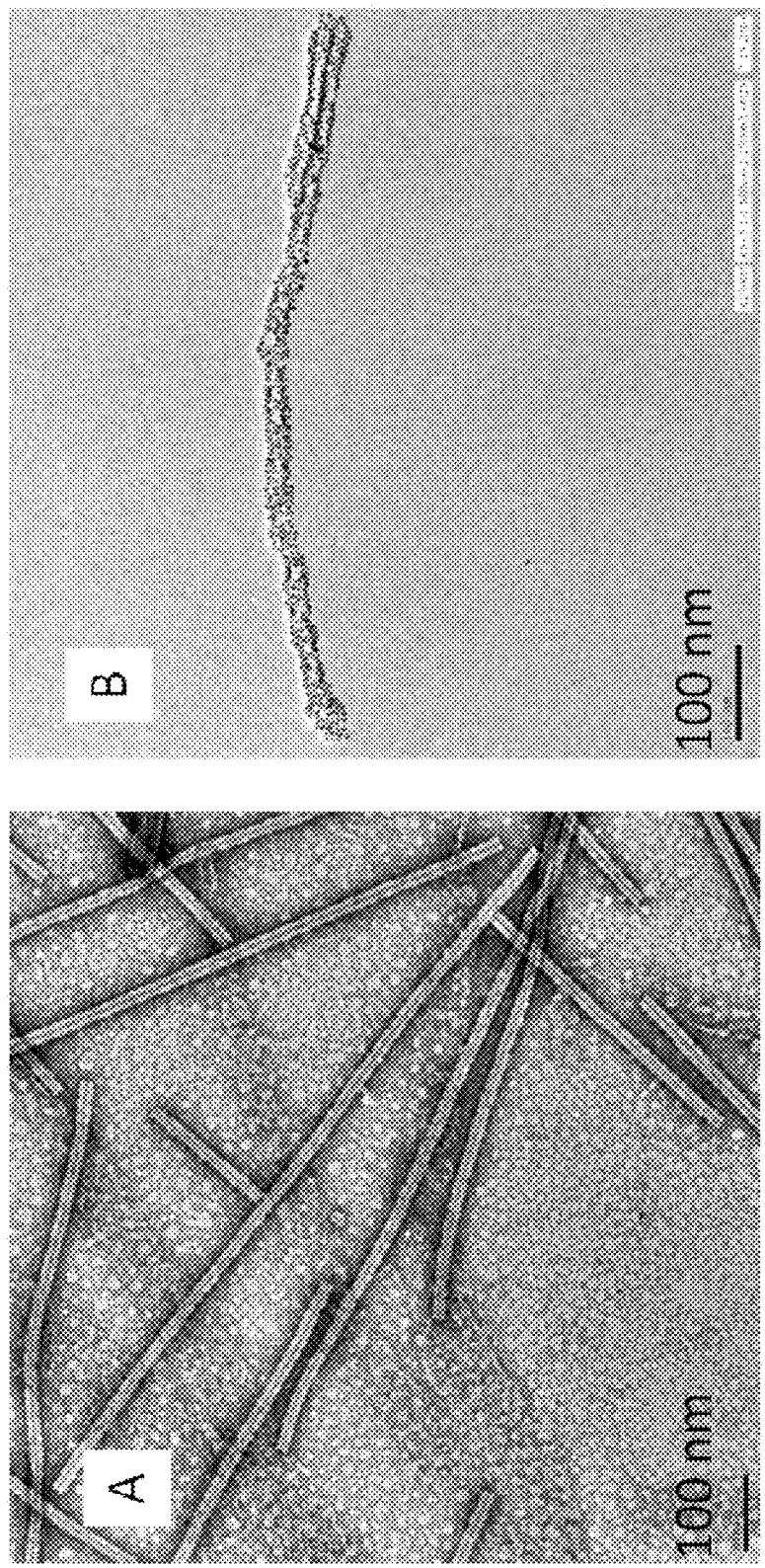
FIG. 9 shows TEM images of His-TMV-CP rods and rod-Au complexes.

FIG. 9 shows TEM images of His-TMV-CP rods and rod-Au complexes. FIG. 9A shows His-TMV-CP rods that were assembled in solution at 400 mM buffer concentration pH 5.0 and stained with uranyl acetate for visualization purposes. FIG. 9B shows His-TMV-CP rods after reaction with Ni-NTA-Nanogold and the sample was not stained; the dark spots correspond to 5 nm gold. This clearly establishes that the 5 nm gold attaches to the His-tag of the protein.

More Complex Structures and Applications of TMV Nanoresonators

More complex resonator structures can be assembled by utilizing the process described above. For example, the structures using His-TMV-CP metal nanoparticle decorated (metalized) disks can be expanded to include the concept of coupling two metalized TMV disks parallel with one another (as seen in FIG. 1) to create optically broad band circuit elements in an ABBA configuration (dual plasmonic ring TMV resonators) with the A sides of the coupled structure containing the metal nanoparticles. Further modification to the metal nanoparticles composing an A side can be accomplished by partial or complete nanoparticle attachment using plating techniques. The coupled ABBA configuration adds capacitance to the structure increasing the magnitude of the response and the spectral location of the response from the single disk resonator. Adjusting the spacing between the A layers containing the metal nanoparticles is a mechanism to further adjust the capacitance. By utilizing the random nature of the location of gaps between metal nanoparticles in the coupled plasmonic ring resonator system, which will shift the location of the optical resonance of the composite structure, an ensemble of these ABBA type resonators is expected produce a broad band optical (electric and magnetic) response. The magnitude of the optical response of an ensemble can be increased by increasing the density of the ABBA structures composing the ensemble, noting that the volume of an ABBA structure responsible for the response is approximately 25,000 times smaller than the volume of the wavelength of light at 500 nm, many such resonators can be placed within small well defined regions within a device.

Switching and/or tuning of the electronic and magnetic response of the structures should be possible by the addition of one or more semiconductor nanoparticles to the decorated TMV nanoparticle disks. Application of a secondary (external) source of excitation to the semiconductor nanoparticle(s) can be used to change the number of electrons within the semiconductor nanoparticle(s), thereby modifying the permittivity and permeability within a ring, changing the spectral resonant response of the ring and coupled structures described above. The amount of secondary excitation, such as by the use of the change in intensity of a laser tuned to an above bandgap semiconductor nanoparticle absorption band, can be used for switching on or off structures, or to provide change to the resonant properties of the structures, in real time (psec response) to actively tune the response. Semiconductor nanoparticle excitation can also be used to modify the capacitance of ABBA structures, further tuning the resonant properties of an individual ABBA structure and/or that of an ensemble device. Optical gain can be induced by the addition of fluorophores (dyes, nanoparticles) to an element or the ensemble, resonant with the optical response.

Structures can be excited by a variety of sources, including but not limited to natural light, laser light, and an electric field.

The utilization of protein-based nanostructures for the synthesis of disk- and rod-like structures offers the possibility of positioning control of inorganic elements at discrete sizes. This approach offers the advantage over the use of synthetic polymers of providing a unique molecular size as dictated by the encoded genes in designed clones. Protein production by means of *E coli* fermentations offers the advantage of scalability, fast production, low cost, and low toxicity.

Plasmonic nanoclusters have been described in Urban et al., "Three-Dimensional Plasmonic Nanoclusters" *Nano Lett.*, 2013, 13 (9), pp 4399-4403. However, these nanoclusters lack an organized central scaffold as described herein. Thus, they lack symmetry and consistent inter-particle distance. It appears difficult to purify quantities of clusters having the same properties using the techniques of this document.

Virus Capsids as Scaffolds

Virus-like particles are viral capsids (including genetically and/or chemically modified versions thereof) lacking their usual nucleic acid core, optionally replaced with an engineered payload, and are described in Douglas, T.; Young, M. "Viruses: Making friends with old foes." *Science* 2006, 312, 873-875; Montague et al., "Recent advances of cowpea mosaic virus-based particle technology" *Human Vaccines* 7:3, 383-390; March 2011; and Lee et al. "Viruses and Virus-Like Protein Assemblies—Chemically Programmable Nanoscale Building Blocks" *Nano Res* (2009) 2: 349 3649, each of which is incorporated herein by reference for teaching methods of preparing and using virus-like particles. Such virus-like particles are typically non-infectious.

In embodiments, a nanocluster includes a viral capsid serving as a scaffold supporting a plurality of metal nanoparticles. The capsid may be that of a virus-like particle or that of a virus (including genetically and/or chemically modified versions thereof). Suitable sources of such capsids include TMV, cowpea mosaic virus (CPMV), cowpea chlorotic mottle virus (CCMV), simian virus 40, and other viruses known in the art. In further embodiments, the capsid is modified to include a plurality of thiols to enhance binding of suitable nanoparticles, for example by genetic engineering to incorporate cysteine residues.

Plasmonic nanoclusters have been described in Urban et al., "Three-Dimensional Plasmonic Nanoclusters" *Nano Lett.*, 2013, 13 (9), pp 4399-4403. However, these nanoclusters lack an organized central scaffold as described herein. Thus, they lack symmetric placement of the metallic nanoparticles and have inconsistent inter-particle distance. Furthermore, it appears difficult to purify quantities of clusters having the same properties using the techniques of this document.

Protein-Based Optical Elements Using Cowpea Mosaic Virus

The protein capsid of cowpea mosaic virus (CPMV) may serve as a viral scaffold. The CPMV capsid has a diameter of approximately 30 nm with icosahedral symmetry. In comparison to the TMV protein disks of about 18 nm, the larger size of CPMV can be preferred for use as optical elements, particularly for applications in the visible spectrum.

Moreover, the CPMV capsid offers two major and previously uncontemplated advantages for use as a protein scaffold for optical elements as compared to TMV. First, the "three dimensional" structure of CPMV as compared to the flat disc of TMV means that structures derived from CPMV can function in practically any orientation. This eliminates a need to accurately position and align protein scaffolds. Second, CPMV serves as a pre-completed structure that is more stable than an assembly of TMV proteins, with demonstrated stability through broad ranges of temperature, pH, buffer, and organic solvents.

Aspects of the work described below on CPMV may be employed in conjunction with other viruses and virus-like particles, for example a non-infectious form of CPMV.

Figure 10A:
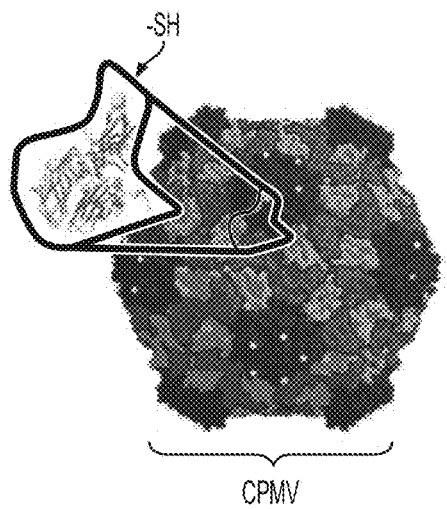
FIG. 10A shows the BC-CPMV protein capsid structure, with the inset depicting the protein subunits and emphasizing a single cysteine (thiol containing amino acid) at the BC-loop resulting in a total of 60 thiols per capsid.

The wild-type chain 1 (small subunit) of CPMV (SEQ ID NO: 6) was modified by a S25C point mutation to create a BC loop cysteine mutant CPMV (SEQ ID NO: 7), thus presenting a total of 60 thiols per capsid, organized in clusters of five located at the 12 vertices of the icosahedron, seen in FIG. 10A. These clusters of thiol groups are suitable for binding metallic nanoparticles, particularly gold nanoparticles, most preferably gold nanospheres, with a preferred size range of about 15 nm to 35 nm. Other modifications to CPMV are contemplated, for example inserting a polyhistidine tag (e.g., 4, 5, 6, 7, or 8 histidine residues) in the BC loop (for example at residue 25) may render the CPMV capable of binding other forms of nanoparticles. It is also possible to use native or genetically engineered amines to incorporate thiols and/or use chemical methods to incorporate reactive groups. For example, one can use click chemistry to add thiols. See Blum et al., "Templated self-assembly of quantum dots from aqueous solution using protein scaffolds" Nanotechnology 17 (2006) 5073-5079 and Medintz et al., "Decoration of Discretely Immobilized Cowpea Mosaic Virus with Luminescent Quantum Dots" Langmuir 2005, 21, 5501-551.

The article Wang, Q., Lin, T., Tang, L., Johnson, J. E., and Finn, M. G. (2002). "Icosahedral virus particles as addressable nanoscale building blocks," *Angew. Chem. Int. Ed.* 41, 459-462 described binding of a thiol-modified CPMV protein to 1.4 nanometer gold particles. However, gold particles of such size are too small to produce the desired optical effects. Indeed, testing with 2 nm and 5 nm found that the particles were too small to produce the desired optical effects. Laboratory experiments and computer modeling indicate that preferred sizes of metal particles are 15-35 nm, more preferably 17-35 nm, even more preferably 20-35 nm.

Nanocluster Assembly and Purification

To prepare gold nanospheres (NS), first 0.9 g of sodium citrate tribasic dihydrate was mixed with 50 ml of Milli-Q water. Depending on the age of the water used the pH of the sodium citrate solution may change over time affecting the resulting size of the NS. It was found that optimally the solution was the one prepared one day before Au-NP synthesis with Milli-Q water pH ~6. (Milli-Q water stored in a sealed glass bottle at room temperature (RT) for more than a week). Upon dilution of the 60 mM SC solution (pH 8.3) to 2.2 mM with Milli-Q water, the pH of the resulting SC solution was measured as 7.3.

Gold nanospheres were produced using a variation of the method described in N. G. Bastús, J. Comenge, V. Puntes, *Langmuir* 2011, 27, 11098, known as the "Puntes method." Specifically, 5.5 ml of 60 mM sodium citrate was diluted to 2.2 mM in a final volume of 150 ml with Milli-Q water in a round bottom flask equipped with Teflon stir bar and a condenser (closed system to avoid evaporation). The solution was heated for 15 min using a stirrer and upon boiling, 1 ml of 25 mM hydrogen tetrachloroaurate (III) in water was added ($HAuCl_4.3H_2O$: Sigma-Aldrich St. Louis, Mo.; 25 mM stock solution was aged for more than one month at RT in the dark prior to use). After 10 min boiling, the color of the solution changed from yellow to gray to pink. The temperature was decreased to 90° C. after which 1 ml of the RT 60 mM sodium citrate was added and stirred for 2 min, then 1 ml of $HAuCl_4$ 25 mM was added to the mix. The solution was stirred vigorously at 90° C. for 30 min. The resulting Au NS dispersion was cooled down at RT overnight. For long term storage, the NS dispersion was kept in the dark at 4° C. The NS dispersion was aged for at least one week prior to reactions with BC-CPMV. NS size was determined by dynamic light scattering (DLS) and transmission electron microscopy (TEM) and the concentration in particles/ml was determined from its absorbance at 525 nm by using a calibration curve prepared with NS controls of known concentration.

BC loop cysteine mutant CPMV was cloned and inoculated into plants as described by Q. Wang, E. Kaltgrad, T. Lin, J. E. Johnson, M. G. Finn, *Chem. Biol.* 2002, 9, 805 and references cited therein. Mutant CPMV was propagated by grinding infected tissue with diatomaceous earth and lightly rubbing the lysate onto seven-day old plants. Infected leaves were harvested and frozen at −80° C. two weeks after inoculation.

The reactive cysteine mutant particles were prone to irreversible precipitation, therefore it was important to do each step as quickly as possible and to keep the samples at 4° C. throughout the purification. Frozen tissue was crushed by hand and blended in a Warring blender (Warring, New Hartford, Conn.) in virus buffer, 0.1 M $NaPO_4$ pH 7.0 with 10 mM DTT (dithiothreitol (DTT), Akron Biotech, Boca Raton, Fla.) The whole cell lysate was centrifuged for 15 minutes at 10,000 g to pellet insoluble plant tissue. The supernatant was filtered through cheese cloth and 0.7 times the volume of 1:1 chloroform:butanol was added and stirred for 30 minutes. The mixture was centrifuged at 10,000 g for 15 minutes and the top aqueous layer was collected. BC-CPMV was precipitated by adding 20% PEG 6,000/1M NaCl to the aqueous layer to reach a final concentration of 5% PEG 6,000/0.25 M NaCl in the solution. The mixture was incubated at 4° C. for 30 minutes followed by centrifugation (30 min, 15,000 g, and immediately resuspended in virus buffer. The pellet containing BC-CPMV was resuspended in virus buffer and centrifuged again at 20,000 g for 15 minutes to remove insoluble material. The supernatant virus was pelleted in an ultracentrifuge at 45,000 rpm in a 50.2 Ti rotor (Beckman Coulter, Inc, Brea, Calif.) for 2.5 hours and immediately resuspended in the virus buffer. The BC-CPMV solution was then loaded onto a 10-40% w/v sucrose gradient and spun at 28,700 g in a SW 32 Ti rotor (Beckman Coulter, Brea, Calif.) for 2 hours. Visible BC-CPMV bands were collected into sterile tubes and stored at 4° C. The concentration of virus was kept below 1.0 mg/ml to prevent aggregation. The concentration of BC-CPMV is determined from the absorbance peak at 260 nm ((absorbance at 260 nm)/8=concentration of virus in mg/ml).

CPMV stability and aggregation were analyzed using a superpose 6 10/300 GL chromatography column on an AKTA purifier (GE Healthcare, Piscataway, N.J.) Roughly 100 μg of each sample was diluted to 500 μL and filtered using 0.22 μm spin filters (EMD Millipore, Billerica, Mass.) prior to running at 1.0 ml/min with a 0.1 M sodium phosphate buffer pH 7.0 (without DTT) mobile phase.

For long term storage, BC-CPMV is stored at 4° C. at concentrations of 0.2-0.5 mg/ml in 10 mM DTT, 10 mM sodium phosphate buffer, 140 mM NaCl, pH 7.2, 15% sucrose as a storage buffer. Just before the reaction with NS, 100 μl of 0.25 mg/ml BC-CPMV (in the storage buffer) was diluted up to 1.5 ml with 10 mM potassium phosphate (KP), pH 6.0. The solution was filtered via a syringe filter (0.2 μm, 25 mm PES-polyether sulfone membrane, Fisher Scientific, Pittsburgh, Pa.). Then 1.5 ml of filtered BC-CPMV was loaded in a pre-packed Hi-Trap Desalting Column (GE Healthcare Biosciences, Piscataway, N.Y.) pre-equilibrated in 10 mM KP pH 6.0. The flow through is discarded and the BC-CPMV is found in the first 1.5 ml elution and concentration determined by its absorbance at 260 nm.

For reacting NS and BC-CPMV, a 40 ml aliquot of NSs ($3\times10^{11}$ particles/ml) prepared by as described above was concentrated to 600 μl using 100 k MWCO concentrators (Amicon Ultra-15, Fisher Scientific) by centrifuging at 4,000 rpm for 2 min at RT (Eppendorf Centrifuge 5810 R equipped with a swing-bucket rotor). In this example 1171 μl of the NSs filtrate recovered after concentration was mixed with a solution containing 200 μl of 100 mM KP pH 6.0, 4 μl of 500 mM EDTA (ethylenediaminetetraacetic acid, serving as a chelator) pH 6.0, and 25 μl of 0.02 mg/ml BC (from Hi-Trap column in 10 mM KP pH 6.0). The use of a chelator was both found to be critical for obtaining the best results from this technique. Pre-concentrating the prepared NSs was also beneficial. The concentrated NSs (600 μl) dispersion was added to the solution containing BC in 50 μl increments with manual mixing by inverting the tube between additions. The reaction was incubated at RT in the dark for 36 h.

Basic water was prepared by adding μl amounts of 2 M KOH to Milli-Q water. The optimum working pH was between 8.5-9.0. To 2 ml of basic water in a 20 mL glass vial containing a Teflon stir bar, 10 μl of 20 mM thioctic acid (TA Fisher Scientific; dissolved in 8:2 v/v ethanol:water) was added. The contents were stirred vigorously using a magnetic stirrer. The reaction mixture was added slowly to the stirred basic water/TA mix in 100 μl increments and stirring was continued at RT for 4 h. Slow addition was found to be required for obtaining best results. The reaction mix after TA treatment was stored overnight at 4° C. The next day, 200 μl of 10× Tris-borate-EDTA buffer (10×TBE: 890 mM Tris, 890 mM boric acid, 20 mM EDTA (pH 8.0)) were added to the reaction mix and concentrated to 500 µl using the 100 k concentrators. A 50 µl aliquot of 50:50 v/v glycerol in water was added and 60 µl of the mixture were loaded per well into a 1% low melting agarose/1×TBE electrophoresis gel. The gel was run at 100 V until a clear separation between the free NSs and BC-Au bands was achieved. This can be seen visually without need of staining the gel since the NSs have a distinct red color.

The BC-Au bands were cut from the gel (~200 mg gel/band) and transferred to a 2 ml Eppendorf tube. Gel pieces were equilibrated in 10 mM Bis-Tris, 1 mM EDTA, pH 6.5 buffer by adding 400 µl the buffer and incubating for 30 min at RT. (This was done 2× and buffer was discarded after each incubation). After buffer equilibration the agarose was melted at 70° C. for 5 min. The agarose was cooled down to 42° C. for 10 min, after which 2 µl of β-agarase enzyme (1000 units/ml, New England Biolabs, Ipswich, Mass.) were added and mixed gently. The enzymatic reaction was carried at 42° C. for 4 h followed by an overnight incubation at RT. After digestion the mixture was stored at 4° C. until ready to use. Prior to characterization the digested agarose was washed with Milli-Q water 2× using the 100 k centrifugation filters to remove any agarose residue and to exchange to water prior to UV-vis, DLS, and TEM characterization. For negative controls, a similar procedure was used to recover free NSs from corresponding gel pieces. Free NSs were characterized as well via DLS, TEM, and UV-vis spectroscopy. Number of particles per ml in NCs and free NSs was calculated from UV-vis data using calibration curves. Calibration curves from control NSs were used.

A related technique for preparing gold-virus complex is described in Soto et al., "Separation and recovery of intact gold-virus complex by agarose electrophoresis and electroelution: Application to the purification of cowpea mosaic virus and colloidal gold complex" *Electrophoresis* 2004, 25, 2901-2906.

Effects of Varying Conditions on Nanocluster Assembly and Purification

For optimization purposes, NS/BC ratios (120, 240, 600, and 2400 NS/virus), pH (4.5 to 7.0), temperature (RT, 37° C., and 42° C.), buffer concentration (8.7, 10, 16, 27.8, 43, 50, and 100 mM) and buffer type (2-(N-morpholino)ethanesulfonic acid (MES), KP, and citrate) were varied in separate experiments using agarose electrophoresis as the tool to determine success. The optimum NS/virus ratio was determined to be 240 (20× excess where 12 NSs/capsid corresponds to 1×). The ideal buffer conditions were 10 mM potassium phosphate pH 6.0 at RT. NS binding to the capsid was optimal when the NS dispersion was concentrated prior to reaction such that a 20×NS level occurred in the final reaction mix. Higher concentrations of NS (>$10^{13}$ particles/ml) promoted significant aggregation, seen as a band that stays in the well during electrophoresis.

The fashion in which the virus binding reaction was performed was explored as well. An "inverted" method of mixing the components (i.e., add NSs to a pre-diluted virus in 10 mM KP pH 6.0, 1 mM EDTA as opposed to adding the virus to the concentrated NS dispersion) was tested and found to provide better results than adding the virus concentrated (0.02 mg/ml) to the NS mix. After the reaction was completed the capping agent thioctic acid (TA) was pre-diluted in basic water (pH 8.5-9.0) and stirred constantly using a magnetic stirrer during the addition of the reaction mix to the TA/basic water mix. Pre-dilution of the TA is critical for avoiding the aggregation of the assemblies. Adding TA concentrated (20 mM) to the reaction mix tends to promote aggregation.

For purification of the nanoclusters, electroelution was attempted to recover the NC, but this gave samples that were not clean enough for our analysis. As an alternative, use β-agarase to break down the agarose prior to the recovery of the NC was attempted. The recovery of the NC using β-agarase was more efficient, since substantially all NCs were recovered from the gel band, and were cleaner in comparison to the electroelution.

Different sources and sized nanospheres were examined. Based on COMSOL simulation, the most desirable candidates were identified as capsid assemblies decorated with 30 nm NS. When commercial 30 nm NS dispersions were tested at the optimum reaction conditions determined for the smaller NS, not much coverage was achieved, possibly due to additives in the commercial products. Therefore, NSs were prepared in-house. In addition to the published Puntes method mentioned above, the conventional method published as J. Schmitt, G. Decher, W. J. Dressick, S. L. Brandow, R. E. Gee, R. Shashidhar, J. M. Calvert, *Adv. Mater.* 1997, 9, 61 was used. Both methods gave better reactivity in comparison to the commercial NS dispersions (from SPI, TedPella, and Nanopartz). Results from the in-house conventional method were encouraging, but the size of the NS synthesized by this method (17-20 nm) were not as large as desired. Using the above-described variation of the Puntes method resulted in larger and near monodisperse NSs. In addition, the NSs resulting from this method were the most reactive toward the virus, among all tested NSs. Nanospheres of 30 nm and 34 nm size were prepared and found to have similar characteristics when formed into nanoclusters.

A series of experiments using various concentrations of EDTA were monitored by DLS. The addition of EDTA up to 5 mM desirably increased the reactivity of the NSs. However, 1 mM EDTA was selected as the concentration for future preparations because that 2 mM and 5 mM EDTA were detrimental to the NS dispersions over time, causing aggregations. TEM data indicated that reactions ran in 1 mM EDTA produced the cleanest NCs in comparison to the ones generated using 5 mM EDTA. The fashion in which the EDTA was added was important as well. The virus tends to aggregate if stock solutions of the virus are exposed to 1 mM EDTA during Hi-Trap columns purification. Also addition of 500 mM EDTA directly to NS dispersions promotes aggregation of NSs. Therefore, the EDTA is mixed with the buffer and NS dispersion filtrate prior to the addition of capsids.

To determine the optimum reaction time, the progress of the reaction was monitored daily for 5 days via DLS. Longer reaction times (>3 days) promoted aggregation resulting in micron-size particles. A series of experiments indicated that reaction times >36 h did not produced better NCs; therefore a 36 hour reaction time was used.

Results

Figure 10B:
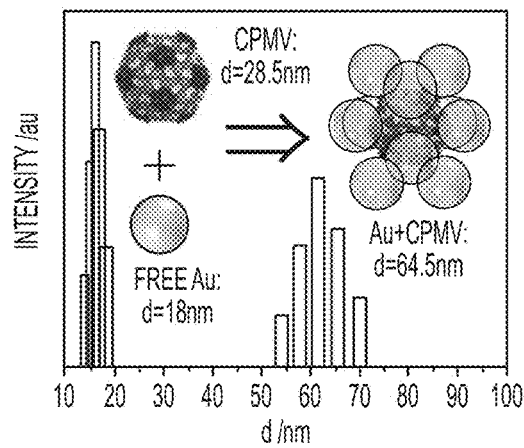
FIG. 10B shows a representative dynamic light scattering spectrum at completion of self-assembly of the nanoclusters (NCs) using 17 nm gold nanospheres (NSs). The inset schematic depicts the NC self-assembly reaction with free gold binding to CPMV capsid.
Figure 10C:
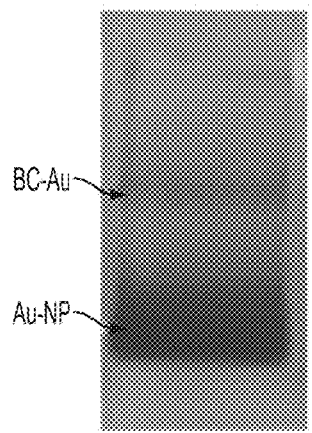
FIG. 10C shows results of agarose electrophoresis of the reaction mix. The lower band is dark red and corresponds to free gold nanoparticles (Au-NP), while the upper band is purple band and corresponds to gold-coated capsid (BC-Au).
Figure 10D:
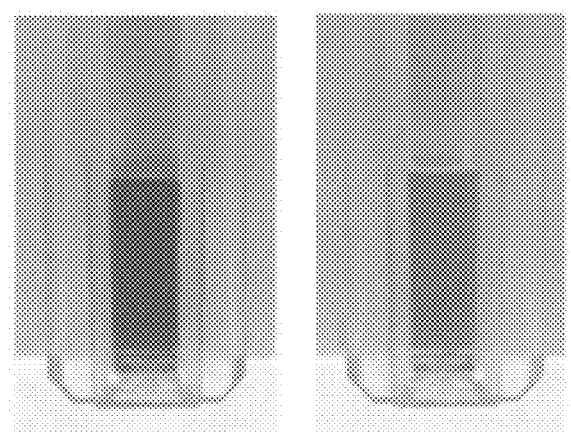
FIG. 10D is an image of free Au-NP (left, a red solution) and BC-Au (right, a purple solution) after extraction from an agarose gel and washing with water.

FIG. 10A shows the BC-CPMV protein capsid structure, with the inset depicting the protein subunits and emphasizing a single cysteine (thiol containing amino acid) at the BC-loop resulting in a total of 60 thiols per capsid. FIG. 10B shows a representative dynamic light scattering spectrum at completion of self-assembly of the nanoclusters (NCs) after 36 hours for the NC self-assembly reaction using 17 nm gold nanospheres (NSs). The inset schematic depicts the NC self-assembly reaction with free gold binding to CPMV capsid. FIG. 10C shows results of agarose electrophoresis of the reaction mix. The lower band is dark red and corresponds to free gold nanoparticles (Au-NP), while the upper band is purple band and corresponds to gold-coated capsid (BC-Au). FIG. 10D is an image of free Au-NP (left, a red solution) and BC-Au (right, a purple solution) after extraction from an agarose gel and washing with water.

Figure 11A:
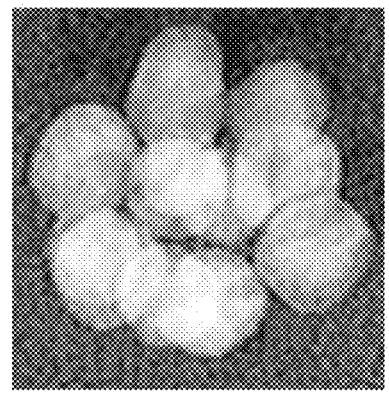
FIG. 11A is a representative transmission electron microscope image of a nanocluster formed from eleven 18 nm diameter Au-NP attached to a capsid.
Figure 11B:
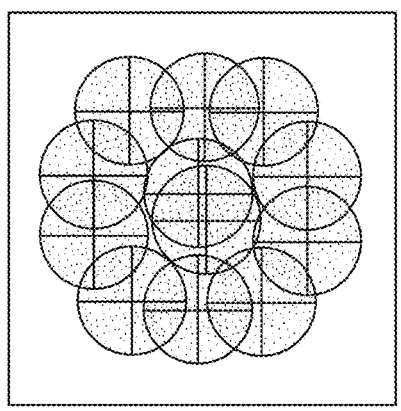
FIG. 11B schematically illustrates the icosahedral symmetry with a 5-fold rotation axes of the nanocluster. The bulk experimental absorbance spectra from free Au and nanocluster (Au-CPMV) suspensions in water is shown in FIG. 11C. The simulated (solid line) and experimental (dashed line) normalized absorbance spectra for 30 nm diameter gold BC-Au is presented in FIG. 11D.
Figure 11C:
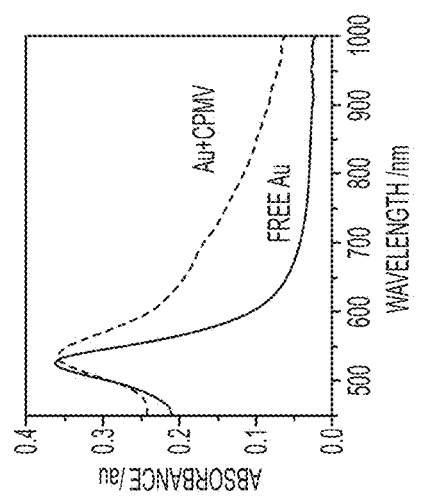
Figure 11D:
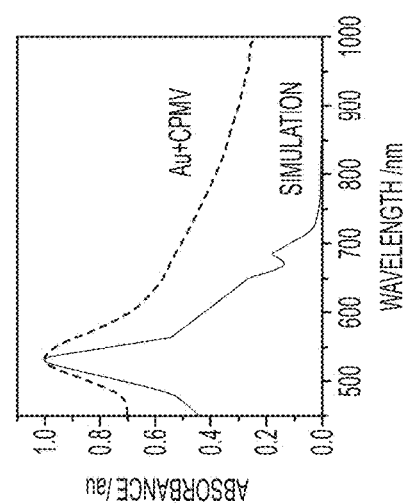

FIG. 11A is a representative transmission electron microscope image of a nanocluster formed from eleven 18 nm diameter Au-NP attached to a capsid. FIG. 11B schematically illustrates the icosahedral symmetry with a 5-fold rotation axes of the nanocluster. The bulk experimental absorbance spectra from free Au and nanocluster (Au-CPMV) suspensions in water is shown in FIG. 11C. The BC-Au absorbance changes significantly from the isolated free Au-NP absorbance. The absorbance peak at 524 nm red-shifts to 535 nm and broadens going from the free Au-NP to the nanocluster suspension. From 600 nm and longer wavelengths a shoulder develops in the nanocluster absorbance spectrum. There is also the emergence of another peak at approximately 675 nm. Using the virus-nanosphere structure presented in FIG. 11B, finite-element simulations were undertaken using COMSOL Multiphysics 4.3b to retrieve the absorbance spectrum for the virus-nanosphere clusters in aqueous suspension for direct comparison to experimental results. The simulated (solid line) and experimental (dashed line) normalized absorbance spectra for 30 nm diameter gold BC-Au are presented in FIG. 11D. The absorbance peak maximum for the simulation occurs at 531 nm and 535 nm for the experiment. Both spectra show a broad shoulder developing around 550 nm and continuing to longer wavelengths. A Fano-like resonance that occurs at 685 nm in the simulated spectrum and also appears in the experimental spectrum at 675 nm. The experimental spectrum is broader overall with respect to the simulation results, presumably from a broader distribution in the experimental sample arising from differences in the saturation levels of the BC-Au in the mixture. Interestingly, both the experimental sample (purple line) and the simulation spectra (black like) show similar features (FIG. 11D).

Figure 12A:
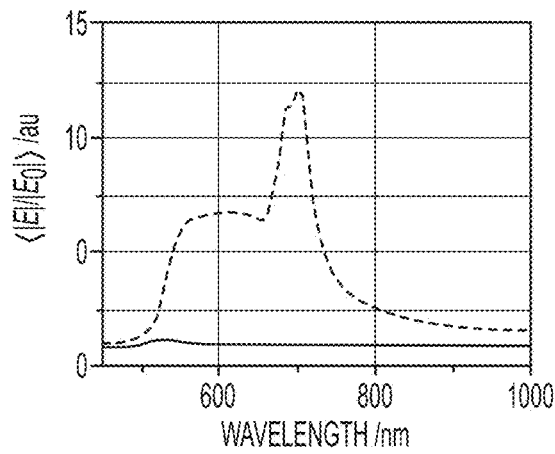
FIG. 12A shows calculated surface-averaged electric fields for twelve 30 nm diameter Au nanospheres (NSs) attached to the capsid (dashed line) and one 30 nm diameter NS attached to the virus (solid line).
Figure 12B:
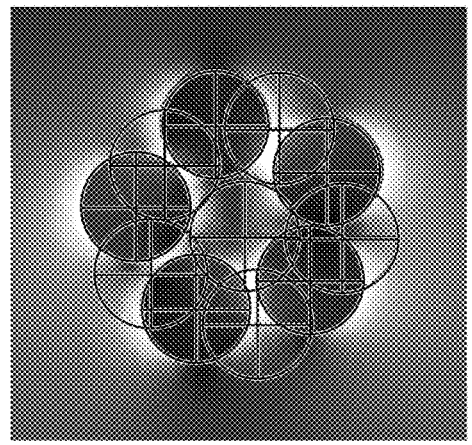
FIG. 12B schematically illustrates a plane slicing through the fully assembled NC showing the electric field distributions.
Figure 12C:
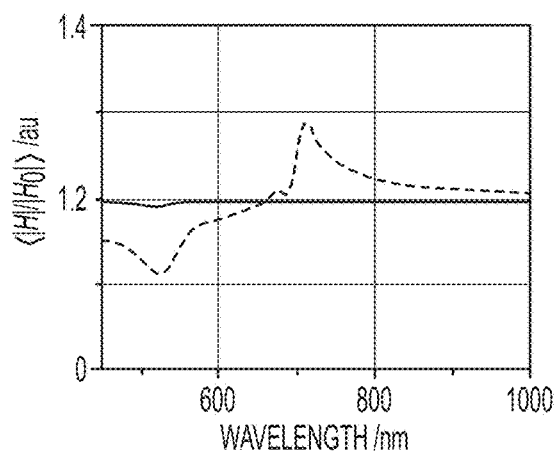
FIG. 12C shows calculated surface-averaged magnetic fields for the fully assembled nanocluster (NC) (dashed line) and one 30 nm diameter NS attached to the scaffold (solid line).
Figure 12D:
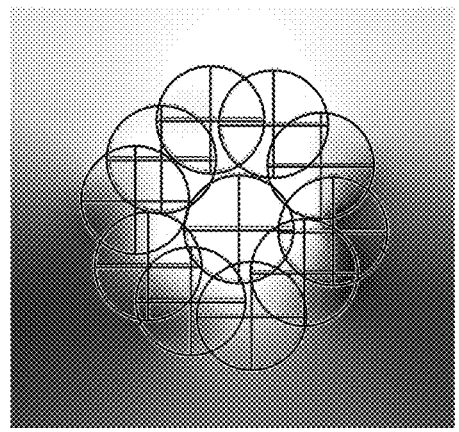
FIG. 12D schematically illustrates a plane slicing through the fully assembled NC showing the magnetic field distributions.

FIG. 12A shows calculated surface-averaged electric fields for twelve 30 nm diameter Au nanospheres (NSs) attached to the capsid (dashed line) and one 30 nm diameter NS attached to the virus (solid line). FIG. 12B schematically illustrates a plane slicing through the fully assembled NC showing the electric field distributions. FIG. 12C shows calculated surface-averaged magnetic fields for the fully assembled nanocluster (NC) (dashed line) and one 30 nm diameter NS attached to the scaffold (solid line). FIG. 12D schematically illustrates a plane slicing through the fully assembled NC showing the magnetic field distributions.

Thus, described herein is a self-assembly strategy to create 3D, icosahedral plasmonic NCs. In situ dynamic light scattering experiments confirm the NS-virus assembly. TEM images demonstrate the NSs to be assembled at fixed locations on the icosahedral virus's surface. Measured bulk absorbance from aqueous suspensions of NCs reproduced the major features of the expected spectrum arrived at via 3D finite-element simulations. Furthermore, because the viruses are easily produced in gram quantities, the self-assembly process is capable of high-throughput, providing a strategy to realized macroscopic quantities for metamaterial applications.

All publications mentioned herein are hereby incorporated by reference for the purpose of disclosing and describing the particular materials and methodologies for which the reference was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

ADDITIONAL REFERENCES

1. Andrea Alù, Engheta N. (2009) The quest for magnetic plasmons at optical frequencies. OPTICS EXPRESS 17, 5723-5731
2. Shafiei F., Monticone F., Le K. Q., Liu X.-X., Hartsfield T., Alu A., Li X. (2013) A subwavelength plasmonic metamolecule exhibiting magnetic-based optical Fano resonance. Nat Nano 8, 95-99
3. Urzhumov Y. A., Shvets G., Fan J., Capasso F., Brandl D., Norlander P. (2007) Plasmonic nanocluster: a path towards negative-index materials. Optics Express 15, 14129
4. Johnson J., Lin T., Lomonossoff G. (1997) Presentation of heterologous peptides on plant viruses: Genetics, structure, and function. Annu. Rev. Phytopathol. 35, 67-86
5. Toussaint L., Bertrand L., Hue L., Crichton R. R., Declercq J. P. (2007) Hight-resolution X-Ray structures of human apoferritin H-chain mutants corrrelated with their activity and metal-binding sites J. Mol. Biol. 365, 440-452

---

SEQUENCE LISTING

<160> NUMBER OF SEQ ID NOS: 7

<210> SEQ ID NO 1
<211> LENGTH: 34
<212> TYPE: DNA
<213> ORGANISM: Artificial Sequence
<220> FEATURE:
<223> OTHER INFORMATION: primer

<400> SEQUENCE: 1
gattcgtttt acatatgtct tacagtatca ctac 34

<210> SEQ ID NO 2
<211> LENGTH: 54
<212> TYPE: DNA
<213> ORGANISM: Artificial Sequence

```
<220> FEATURE:
<223> OTHER INFORMATION: primer

<400> SEQUENCE: 2
tagtaccatg gtcattagtg atggtgatgg tgatgagttg caggaccaga ggtc        54

<210> SEQ ID NO 3
<211> LENGTH: 159
<212> TYPE: PRT
<213> ORGANISM: Artificial Sequence
<220> FEATURE:
<223> OTHER INFORMATION: synthetic construct

<400> SEQUENCE: 3

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Gly Pro Ala Thr
145                 150                 155

<210> SEQ ID NO 4
<211> LENGTH: 170
<212> TYPE: PRT
<213> ORGANISM: Artificial Sequence
<220> FEATURE:
<223> OTHER INFORMATION: synthetic construct

<400> SEQUENCE: 4

Glu Gly Asp Ile His Met Ser Tyr Ser Ile Thr Thr Pro Ser Gln Phe
1               5                   10                  15

Val Phe Leu Ser Ser Ala Trp Ala Asp Pro Ile Glu Leu Ile Asn Leu
            20                  25                  30

Cys Thr Asn Ala Leu Gly Asn Gln Phe Gln Thr Gln Gln Ala Arg Thr
        35                  40                  45

Val Val Gln Arg Gln Phe Ser Glu Val Trp Lys Pro Ser Pro Gln Val
    50                  55                  60

Thr Val Arg Phe Pro Asp Ser Asp Phe Lys Val Tyr Arg Tyr Asn Ala
65                  70                  75                  80

Val Leu Asp Pro Leu Val Thr Ala Leu Leu Gly Ala Phe Asp Thr Arg
                85                  90                  95

Asn Arg Ile Ile Glu Val Glu Asn Gln Ala Asn Pro Thr Thr Ala Glu
            100                 105                 110

Thr Leu Asp Ala Thr Arg Arg Val Asp Asp Ala Thr Val Ala Ile Arg
```

```
                    115                 120                 125

Ser Ala Ile Asn Asn Leu Ile Val Glu Leu Ile Arg Gly Thr Gly Ser
            130                 135                 140

Tyr Asn Arg Ser Ser Phe Glu Ser Ser Gly Leu Val Trp Thr Ser
145                 150                 155                 160

Gly Pro Ala Thr His His His His His
                165                 170

<210> SEQ ID NO 5
<211> LENGTH: 170
<212> TYPE: PRT
<213> ORGANISM: Artificial Sequence
<220> FEATURE:
<223> OTHER INFORMATION: synthetic construct

<400> SEQUENCE: 5

Glu Gly Asp Ile His Met Ser Tyr Ser Ile Thr Thr Pro Ser Gln Phe
1               5                   10                  15

Val Phe Leu Ser Ser Ala Trp Ala Asp Pro Ile Glu Leu Ile Asn Leu
            20                  25                  30

Cys Thr Asn Ala Leu Gly Asn Gln Phe Gln Thr Gln Gln Ala Arg Thr
        35                  40                  45

Val Val Gln Arg Gln Phe Ser Glu Val Trp Lys Pro Ser Pro Gln Val
    50                  55                  60

Thr Val Arg Phe Pro Asp Ser Asp Phe Lys Val Tyr Arg Tyr Asn Ala
65                  70                  75                  80

Val Leu Asp Pro Leu Val Thr Ala Leu Leu Gly Ala Phe Asp Thr Arg
                85                  90                  95

Asn Arg Ile Ile Glu Val Glu Asn Gln Ala Asn Pro Thr Thr Ala Glu
            100                 105                 110

Thr Leu Asp Ala Thr Arg Arg Val Asp Asp Ala Thr Val Ala Ile Arg
        115                 120                 125

Ser Ala Ile Asn Asn Leu Ile Val Glu Leu Ile Arg Gly Thr Gly Ser
    130                 135                 140

Cys Asn Arg Ser Ser Phe Glu Ser Ser Gly Leu Val Trp Thr Ser
145                 150                 155                 160

Gly Pro Ala Thr His His His His His
                165                 170

<210> SEQ ID NO 6
<211> LENGTH: 189
<212> TYPE: PRT
<213> ORGANISM: Cowpea mosaic virus

<400> SEQUENCE: 6

Gly Pro Val Cys Ala Gl

Trp Lys Ser Gly Thr Ile His Val Gln Leu Asn Val Arg Gly Ala Gly
 65                  70                  75                  80

Val Lys Arg Ala Asp Trp Asp Gly Gln Val Phe Val Tyr Leu Arg Gln
                 85                  90                  95

Ser Met Asn Pro Glu Ser Tyr Asp Ala Arg Thr Phe Val Ile Ser Gln
            100                 105                 110

Pro Gly Ser Ala Met Leu Asn Phe Ser Phe Asp Ile Ile Gly Pro Asn
        115                 120                 125

Ser Gly Phe Glu Phe Ala Glu Ser Pro Trp Ala Asn Gln Thr Thr Trp
    130                 135                 140

Tyr Leu Glu Cys Val Ala Thr Asn Pro Arg Gln Ile Gln Gln Phe Glu
145                 150                 155                 160

Val Asn Met Arg Phe Asp Pro Asn Phe Arg Val Ala Gly Asn Ile Leu
                165                 170                 175

Met Pro Pro Phe Pro Leu Ser Thr Glu Thr Pro Pro Leu
            180                 185

<210> SEQ ID NO 7
<211> LENGTH: 189
<212> TYPE: PRT
<213> ORGANISM: Artificial Sequence
<220> FEATURE:
<223> OTHER INFORMATION: engineered CPMV

<400> SEQUENCE: 7

Gly Pro Val Cys Ala Glu Ala Ser Asp Val Tyr Ser Pro Cys Met Ile
1               5                   10                  15

Ala Ser Thr Pro Pro Ala Pro Phe Cys Asp Val Thr Ala Val Thr Phe
            20                  25                  30

Asp Leu Ile Asn Gly Lys Ile Thr Pro Val Gly Asp Asp Asn Trp Asn
        35                  40                  45

Thr His Ile Tyr Asn Pro Pro Ile Met Asn Val Leu Arg Thr Ala Ala
    50                  55                  60

Trp Lys Ser Gly Thr Ile His Val Gln Leu Asn Val Arg Gly Ala Gly
 65                  70                  75                  80

Val Lys Arg Ala Asp Trp Asp Gly Gln Val Phe Val Tyr Leu Arg Gln
                 85                  90                  95

Ser Met Asn Pro Glu Ser Tyr Asp Ala Arg Thr Phe Val Ile Ser Gln
            100                 105                 110

Pro Gly Ser Ala Met Leu Asn Phe Ser Phe Asp Ile Ile Gly Pro Asn
        115                 120                 125

Ser Gly Phe Glu Phe Ala Glu Ser Pro Trp Ala Asn Gln Thr Thr Trp
    130                 135                 140

Tyr Leu Glu Cys Val Ala Thr Asn Pro Arg Gln Ile Gln Gln Phe Glu
145                 150                 155                 160

Val Asn Met Arg Phe Asp Pro Asn Phe Arg Val Ala Gly Asn Ile Leu
                165                 170                 175

Met Pro Pro Phe Pro Leu Ser Thr Glu Thr Pro Pro Leu
            180                 185

What is claimed is:

1. A nanocluster comprising:
   a cowpea mosaic virus (CPMV) protein capsid, the protein genetically modified to incorporate a plurality of cysteine residues providing thiol groups on an exterior surface of the capsid, and
   a plurality of metal nanoparticles with a size between 15 nm and 35 nm bound to the thiol groups.

2. The nanocluster of claim 1, wherein twelve clusters of thiol groups are present on said exterior surface of said capsid.

3. The nanocluster of claim 1, wherein said protein comprises SEQ ID No: 7.

4. The nanocluster of claim 1, wherein said metal nanoparticles comprise gold nanoparticles and/or silver nanoparticles.

5. The nanocluster of claim 1, where said metal nanoparticles are gold nanospheres all of approximately the same size.

6. The nanocluster of claim 5, wherein said gold nanospheres have a size between 17 nm and 35 nm.

7. A nanocluster comprising:
   a viral protein capsid comprising thiol groups suitable for binding metallic nanoparticles and
   a plurality of metal nanoparticles with a size between of 15 nm to 35 nm bound to the thiol groups.

8. The nanocluster of claim 7, wherein said viral protein capsid is in a state of being genetically engineered to incorporate additional cysteine residues.

* * * * *